United States Patent [19]
Rothstein et al.

[11] Patent Number: 5,821,094
[45] Date of Patent: Oct. 13, 1998

[54] S-LOCUS RECEPTOR KINASE GENE IN A SELF-INCOMPATIBLE BRASSICA NAPUS LINE

[75] Inventors: Steven J. Rothstein, Guelph; Daphne R. Goring, Woodbridge, both of Canada

[73] Assignee: University of Guelph, Guelph, Canada

[21] Appl. No.: 265,628

[22] Filed: Jun. 24, 1994

Related U.S. Application Data

[63] Continuation of Ser. No. 959,945, Oct. 8, 1992, abandoned, which is a continuation-in-part of Ser. No. 847,564, Mar. 3, 1992, abandoned.

[51] Int. Cl.⁶ .............................. A01H 5/00; C12N 15/29; C12N 15/82
[52] U.S. Cl. ...................... 435/172.3; 435/6; 435/320.1; 536/23.2; 536/23.6; 536/24.3; 536/24.33; 800/205
[58] Field of Search ........................ 800/205; 435/172.3, 435/6, 320.1; 536/23.6, 23.2, 24.3, 24.33; 530/370

[56] References Cited

U.S. PATENT DOCUMENTS 5,053,331  10/1991  Clarke et al. ........................ 435/172.3

FOREIGN PATENT DOCUMENTS

| 0212385 | 3/1987 | European Pat. Off. ........ C12N 15/00 |
| 0436467 | 12/1990 | European Pat. Off. ........ C12N 15/29 |
| 0 519 869 | 12/1992 | European Pat. Off. . |

OTHER PUBLICATIONS

Goring et al. "Brassica napus ssp. oleifera serine/threonine kinase receptor . . . ", *EMBL Sequence Database*, Release 33, AC M97667 (Oct. 5, 1992).
Goring et al. "Use of the polymerase chain reaction to isolate an S–locus . . . ", *Molecular and General Genetics*, 234(2):185–192 (Aug. 1992).
Gouilluy et al. "PCR detection of transcripts homologous to the self–incompatibility . . . ", *Theor. Appl. Genet.*, 82: 466–472 (1991).
Sequence Accession No.: Q 03278, Database n–geneseq 22 (1 Aug., 1990).
Walker et al. (1990) Nature 345:743–746 (June 21).
Fry et al. (1987) Plant Cell Reports 6:321–325.
Lewin (1987) Science 237:1570.
"Molecular cloning of a putative receptor protein kinase gene encoded at the self–incompatibility locus of *Brassica oleracea*," Stein, J.C. et al., Proc. Natl. Acad. Sci., USA 88: 8816–8820, Oct., 1991.
"DNA sequences of self–incompatibility genes from *Brassica campestris* and *B. oleracea*: polymorphism predating speciation," Dwyer, K.G., et al., Plant Molecular Biology 16: 481–486, 1991.
"A new class of S–sequences defined by a pollen recessive self–incompatibility allele of *Brassica oleracea*," Chen, C. and Nasrallah, J.B., Mol. Gen. Genet. 222:241–248, 1990.

"Sequences of S–glycoproteins, products of the *Brassica campestris* Self–Incompatibility Locus," Takayama, S., et al., Nature 326: 102–105, Mar., 1987.
"A cDNA clone encoding S–locus–specific glycoprotein from *Brassica oleracea*," Nature 318: 263–267 Nov. 1985.
"Isolation of a Second S–Locus–related cDNA from *Brassica oleracea*, Genetic Relationships Between the S–Locus and Two Related Loci," Genetics 127: 221–228, Jan., 1991.
"Amino–acid sequences of glycoproteins encoded by three alleles of the S–Locus of *Brassica oleracea*,"Nasrallah, J.B., et al., Nature 326: 617–619, Apr. 1987.
"A Highly Conserved Brassica Gene with Homology to the S–Locus–Specific Glycoprotein Structural Gene," Lalonde, B.A., et al., The Plant Cell 1: 249–258, Feb., 1989.
"The Self–Incompatibility Genes of Brassica: Expression and Use in Genetic Ablation of Floral Tissues,"Nasrallah, J.b., et al., Ann. Rev. Plant Physiol. Plant Mol. Biol. 42: 393–422, 1991.
"A homozygous S–genotype of *Brassica oleracea* express two S–like genes," Trick, M. and Flavell, Mol. Gen. Genet. 218: 112–117, 1989.
"Transformation of *Brassica oleracea* with an S–locus gene from *Brassica campestris* changes the self–incompatibility phenotype," Toriyama, K., et al., Theor. Appl. Genet. 81: 769–776, 1991.
"Activity of an S–Locus Gene Promoter in Pistils and Anthers of transgenic Brassica," Sato, T., et al., The Plant Cell 3: 867–876, 1991.

(List continued on next page.)

*Primary Examiner*—Elizabeth McElwain
*Attorney, Agent, or Firm*—Foley and Lardner

[57] ABSTRACT

The S-locus of Brassica contains the genetic information that encodes for self-incompatibility. In its first aspect, it is directed to an isolated gene, the SRK-910 gene, that segregates with the self-incompatibility phenotype. In its second aspect, the present invention is directed to an isolated cDNA that corresponds to the isolated gene and that has 2749 nucleotides.

The isolated cDNA of the present invention encodes for a protein, i.e., the S-locus receptor kinase-910 protein ("the SRK-910 protein") which is also a part of the present invention. The SRK-910 protein, has 858 amino acids and is encoded for by the first 2575 nucleotides of the isolated cDNA of the present invention.

The present invention is also directed to an oligonucleotide probe that is capable of distinguishing the SRK-910 gene from partially homologous genes at the S-locus that encode for the S-locus glycoproteins.

The present invention is also directed to a transfer vector comprising the cDNA for the SLG-910 allele in combination with the cDNA of claim 1.

Finally, the present invention is also directed to a method for conferring the self-incompatible phenotype on a self-compatible plant comprising transferring the disclosed transfer vector into a plant that is capable of assimilating the transfer vector and expressing self-incompatibility.

14 Claims, 20 Drawing Sheets

OTHER PUBLICATIONS

"Self–Incompatibility: A Self–Recognition System in Plants," Haring, V., et al., Science 250: 937–941, 1990.

"S–Locus–Specific Glycoproteins Associated with Self–Incompatibility in *Brassica campestris*," Isogai, A., et al., Plant Cell Physiol. 28 (7): 1279–1291, 1987.

"Sequences of S–Glycoproteins, products of the *Brassica capestris* Self–Incompatibility Locus," Takayama, et al., Nature, 326: 102–105, 1987.

"Species Crosses Within the Genus Brassica II. Artificial *Brassica napus* L," Olsson, G., Hereditas 46, 351–386, 1960.

"Self–Incompatibility Systems in Angiosperms III. Cruciferae," Bateman, A.J., Heredity, 9: 53–68, 1955.

"Distribution of Self–Incompatibility Alleles and Breeding Structure of Open–Pollinated Cultivars of Brussel Sprouts," Ockendon, D.J., Heredity, 33: 159–171, 1974.

"The Introgression of S–Alleles into Forage Rape, *Brassica napus* L. from Turnip, *Brassica campestris* L. SSP. rapifera," Mackay, G.R., Euphytica, 26: 511–519, 1977.

"Methods of Producing $F_1$ Hybrid Swedes *Brassica napus* SSP rapifera," Gowers, S., Euphytica, 24: 537–541, 1975.

"An S–Allele Survey of Cabbage (*Brassica oleracea* var. Capitata)," Ockendon, D.J., Euphyta, 31: 325–331, 1982.

"Self–Incompatibility proteins in Plants: Detection, Genetics, and Possible Mode of Action," Nasrallah, M.E., et al., Heredity, 25: 23–27, 1970.

"Non–Linear Dominance Relationships Between S–Alleles," Thompson, K.F., et al., Heredity 21: 345–362, 1966.

"Use of a Phage Vector for Rapid Synthesis and Cloning of Single–Stranded cDNA," Bellemare, et al., Gene, 52: 11–19, 1987.

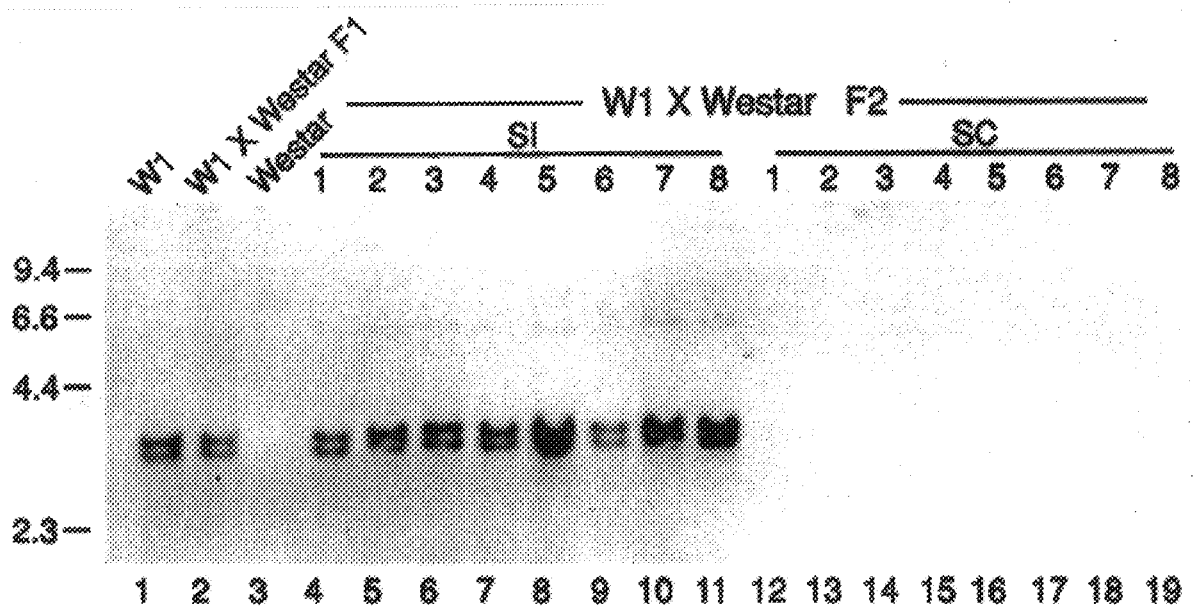

FIG. 4-1

| FIG. 4-1 | FIG. 4-2 |
|---|---|
| FIG. 4-3 | |

```
M  K  G  V  R  K  T  Y  D  S  S  Y  T  L  S  F  L  L  V  F  F
ATGAAAGGAGTAAGAAAAACCTACGATAGTTCTTACACTTTATCCTTCTTGCTCGTCTTTT

E  S  L  T  I  S  N  N  R  T  L  V  S  P  G  N  V  F  E  L  G
GAATCTCTTACAATCTCAAACAACAGAACACTTGTCTCCAGTAATGTCTTGAGCTCGG

P  Y  K  T  Y  V  W  V  A  N  R  D  N  P  L  S  D  S  I  G  T
CCCTATAAAACCTATGTTGGGTTGCAAACAGAGATAACCCTCTCTCCGATTCCATTGGTAC

S  T  N  L  T  R  G  N  E  R  S  P  V  V  A  E  L  L  E  N  G
TCGACGAATCTGACTAGAGGAAATGAGAGATCTCCGGTGGTGGCAGAGCTTCTGGAGAACGG

F  D  F  P  T  D  L  L  P  E  M  K  L  G  Y  D  R  K  K  G
TTCGATTTCCCTACAGATACTTGCTTCCAGAGATGAAACTAGGCTACGACCGCAAAAAGG

S  Y  Q  L  D  T  Q  R  G  M  P  E  F  Y  L  L  K  N  G  V  R
TCGTACCAACTAGACACTCAAAGAGGAATGCCTGAGTTTTATCTATTGAAAAACGGCGTACG

K  L  S  Y  M  V  Y  Y  N  F  T  D  N  S  E  E  A  A  Y  T  F  R
AAGTTGAGTTACATGGTGTACAACTTCACAGATAATAGTGAGGAGGCTGCTTATACATTTCG

R  L  T  F  F  P  T  S  W  E  W  N  L  F  W  T  S  P  E  E  P
CGACTAACGTTCACTCCGACATCATGGGAATGGAACTTGTTCTGGACTTCACCAGAGAGCC

P  V  C  N  C  I  Q  G  F  K  P  F  N  M  Q  Q  W  E  L  R  V
CCAGTGTGTAACTGTATCCAAGGTTTCAAGCCCTTCAATATGCAGCAGTGGGAACTGAGAGT

R  M  K  N  M  K  L  P  E  T  T  M  A  I  V  D  R  S  I  G  R
AGGATGAAAAATATGAAGTTGCCAGAGAACTACGATGGCTATTGTCGACCGCAGTATTGGTCG

D  I  R  N  G  G  S  G  C  V  I  W  T  G  E  L  E  D  I  R  N
GATATCCGGAATGGTGGGTCGGTTGTGATTTGGACAGGAGAGCTTGAGGATATCCGGAA

K  R  N  A  N  G  K  T  I  A  L  I  V  G  V  C  V  L  L  M
AAGAGAAACGCGAATGGAAAACCATAGCGTTGATTGTTGGAGTTTGTGTTCTGCTTCTTAT
```

```
     V  M  F  L  F  H  P  A  L  S  I  H  I  N  T  L  S  S  T
     CGTCATGTTTCTATTTCATCCTGCCCTTTCGATCCATATCAACACTTTGTCGTCTACA    40
                                                                 120

F  F  R  T  S  S  S  R  W  Y  L  G  I  W  Y  K  N  L
     CTTCTTTAGAACCACCTCAAGTTCTCGTTGGTATCTCGGGATATGGTACAAGAATTTG    80
                                                                 240

L  K  I  S  N  M  N  L  V  L  L  D  H  S  N  K  S  V  W    120
     GCTCAAAATCTCCAACATGAACCTTGTCCTCCTCGACCACTCTAATAAATCTGTTTGG   360

N  F  V  I  R  Y  S  N  N  N  A  S  G  F  L  W  Q  S       160
     AAACTTCGTCATTCGATACTCCAATAACAACCAAGTGGATTCTTGTGGCAAAGT       480

L  N  R  F  L  T  A  W  R  N  S  D  D  P  S  S  G  E  I    200
     GCTGAACAGATTCCTTACACAGCATGGAGAAATTCAGATGATCCCTCAAGCGGGAAATC  600

G  Y  R  S  G  P  W  N  G  V  R  F  N  G  I  P  E  D  Q    240
     AGGCTACCGGAGTGGTCCATGGAATGGAGTCCGATTTAATGGCATACCAGAGGACCAA   720

M  T  D  K  S  I  Y  S  R  L  I  I  S  N  D  E  Y  L  A    280
     AATGACCGACAAGAGCATCTACTCGAGATTGATAATAAGTAACGATGAGTATTGGCG    840

E  C  D  V  Y  K  T  C  G  S  Y  A  Y  C  D  V  N  T  S    320
     GGAGTGCGATGTGTACAAGACTTGTGGGTCTTATGCTTACTGTGACGTGAACACATCA   960

W  A  G  G  C  I  R  R  T  R  L  S  C  N  G  D  G  F  T    360
     CTGGGCAGGTGGGTGTATAAGGAGGACGCGGCTTAGCTGCAATGGAGATGGTTTACC   1080

K  E  C  K  K  R  C  L  S  D  C  N  C  T  A  F  A  N  A    400
     GAAAGAATGTAAGAAGAGGTGCCTTAGCAGATCTTAATTGTACCGCGTTTGCAAATGCG  1200

Y  F  D  D  G  Q  D  L  Y  V  R  L  A  A  A  D  L  V  K    440
     TTACTTTGATGACGGTCAAGATCTTTATGTGCGCCTCGCCGCCGCTGATCTCGTTAAA   1320

I  M  F  C  L  W  K  R  K  Q  K  R  A  K  T  T  A  T  S    480
     GATCATGTTCTGCCTCTGGAAAAGAAACAAAAGCGAGCAAAAACAACTGCAACATCT   1440
```

| FIG. 4-1 | FIG. 4-2 |
|---|---|
| FIG. 4-3 | FIG. 4-4 |

```
  I   V   N   R   Q   R   N   Q   D   L   L   M   N   G   M   I   L   S   S   K   R   Q
ATTGTAAATCGACAGAGAAACCAAGATTGCTAATGAACGGATGATACTATCAAGCAAGAGACA

A   V   V   K   A   T   E   N   F   S   N   C   N   K   L   G   Q   G   G   F   G   I
GCTGTTGTCAAAGCCACCGAAAATTTCTCCAATTGTAACAAACTCGGACAAGGTGGTTTCGGTAT

K   T   S   V   Q   G   T   G   E   F   M   N   E   V   R   L   I   A   R   L   Q   H
AAAACGTCGGTTCAAGGACTGGTGAGTTTATGAATGAGGTGAGATTGATCGCGAGGCTTCAGCA

V   Y   E   Y   L   E   N   L   S   L   D   S   Y   L   F   G   N   K   R   S   S   T
GTATATGAGTATTTAGAAAATTTAAGCCTCGATTCTTATCTCTTCGGAAATAAACGAAGCTCTAC

Y   L   H   Q   D   S   R   F   R   I   I   H   R   D   M   K   V   S   N   I   L   L
TATCTTCATCAAGACTCACGGTTTAGATAATCCACAGAGATATGAAAGTAAGTAACATTTTGCT

R   D   E   T   E   A   N   T   R   K   V   G   T   Y   G   Y   M   S   P   E   Y
AGGGACGAGACTGAAGCTAACACAAGGAAGGTGGTCGGAACTTACGGCTACATGTCTCCGGAGTA

V   L   E   I   V   S   G   K   R   N   R   G   F   Y   N   L   N   H   E   N   N   L
GTTCTTGAAATTGTTAGTGGAAAAAGGAACAGAGGATTCTACAACTTGAACCACGAAAACAATCT

P   V   I   V   D   S   L   S   S   L   P   A   T   F   Q   P   K   E   V   L   K   C
CCAGTCATCGTAGATTCATTGTCATCATTACCAGCAACCTTTCAACCAAAAGAAGTTCTAAAATG

S   S   V   V   W   M   L   G   S   E   A   T   E   I   P   Q   P   T   P   P   G   Y
TCGTCCGGTGGTTTGGATGCTTGGAAGTGAAGCAACAGAGATTCCTCAGCCTACACCGCCAGGTTA

D   D   E   S   W   T   V   N   Q   Y   T   C   S   D   I   D   A   R   *
GACGACGAATCCTGGACGGTGAACCAGTACACCTGCTCAGACATCGATGCCCGGTAGTACGAAAT
AGAAAATAAAATTCAATAGTTAAGTTTGTTATTGATAACCAAATCTTGTTATTCCTGGTGGT
```

FIG. 4-4

|   |   |   |
|---|---|---|
| L P I E N K T E E L E L P L I E L E | | 520 |
| GTTGCCTATAGAGAAACAAAACTGAGGAATTGGAACTTCCATTGATAGAGTTGGAA | | 1560 |
| V Y K G R L L D G Q E I A V K R L S | | 560 |
| TGTTTACAAGGGTAGATTACTTGATGGGCAAGAAATTGCGGTAAAAAGGCTATCA | | 1680 |
| I N L V R I L G C C I E A D E K M L | | 600 |
| TATAAACCTTGTCCGAATTCTTGGCTGTTGCATTGAGGCAGACGAGAAGATGCTG | | 1800 |
| L N W K D R F N I T N G V A R G L L | | 640 |
| GTTAAATTGGAAGGACAGATTCAACATTACCAATGGTGTTGCTCGAGGACTTTTA | | 1920 |
| D K N M T P K I S D F G M A R I F A | | 680 |
| TGATAAAAATATGACACCAAAGATCTCGGATTTTGGGATGGCCAGAATCTTTGCA | | 2040 |
| A M D G V F S E K S D V F S F G V I | | 720 |
| CGCAATGGATGGGGTATTCTCGGAAAAATCAGATGTTTTCAGTTTTGGAGTCATT | | 2160 |
| L S Y V W S H W T E G R A L E I V D | | 760 |
| TCTAAGCTATGTGTATGGAGTCACTGGACGGAGGAAGAGCGCTAGAAATTGTTGAT | | 2280 |
| I Q I G L L C V Q E R A E H R P T M | | 800 |
| CATACAAATTGGTCTCTTCTTGTGTTCAAGAACGTGCAGAGCATAGACCAACGATG | | 2400 |
| S L G R S P Y E N N P S S S R H C D | | 840 |
| TTCCCTCGGAAGAACTCCTTATGAAAATAATCCTTCATCAAGTAGACATTGCGAC | | 2520 |
| CCGTTGAGAAGTTCAGATAATTAACTATTGGGTGACCGGATATTATAAGTGAA | | 2640 |
| GTTGTCATATTCGTTTTTCTGAATGAATGTTAAAGTTATTATTC | | 2749 |

FIG. 6

```
Cons.              ------lG-G---G-V------   ------A-K-L------   ------E------   ------L------
SRK-910    ENFSNCNKLGQGGFGIVYKGRLLD   GQEIAVKRLSKTSV   QGTGEFMNEVRLIARL   QHINLVRILGCCIE  594
SRK-6      ENFSsCNKLGQGGFGIVYKGRLLD   GkEIAVKRLSKTSV   QGTdEFMNEVtLIARL   QHINLVqVLGCCIE
SRK-2      EHFSdfNKvGkGGFGvVYKGRLvD   GQEIAVKRLSemSa   QGTdEFMNEVRLmqsf   sHnNLVRlLGCCvy
ARK-1      nNFSNdNKlGQGGFGIVYKGRLLD   GkEIAVKRLSKmSs   QGTdEFMNEVRLiAkL   QHINLVRlLGCCvd
ZMPK-1     rkF  kveLGrGesGtVYKGvLeD   drhvAVKklenvr    QGkevFqaElsvIgRi   nHmNLVRIwGfCsE
                     Domain I                Domain II         Domain III         Domain IV Cons.                                                                    ---G--YL------   ---H-DLKPENI---
SRK-910    ADEKMLVYEYLENLSLDSYLFGNKR   SSTLNWKDRFNITNGVARGLLYLHQDSRFRIIHRDMKVSNILLDKNM  667
SRK-6      gDEKMLiYEYLENLSLDSYLFGktR   rSkLNWneRFdITNGVARGLLYLHQDSRFRIIHRDlKVSNILLDKNM
SRK-2      egEKliYEYLENLSLDShLFdetR    ScmLNWqmRFnIiNGiARGLLYLHQDSRFRIIHRDlKaSNvLLDKdM
ARK-1      kgEKMLiYEYLENLSLDShLFdqtR   SSnLNWqkRFdINGiARGLLYLHQDSRCRIIHRDlKaSNvLLDKNM
ZMPK-1     gshrlLVsEYvENgSLaniLFsegg   niLLdWegrRFNIalGVAkGLaVLHheclewvIHcDvKpeNILLDqaf
                     Domain V                                 Domain VI Cons.      ---I-DFG------            ------GT---Y-APE-              ------D--FS--GV------
SRK-910    TPKISDFGMARIFARDETEA      NTRKVVGTGYGMSPEY               AMDGVFSEKSDVFSFGVIVLEIVSGKRNRGFYN  735
SRK-6      iPKISDFGMARIFeRDETEA      NTmKVVGTGYGMSPEY               AMyGiFSEKSDVFSFGVIVLEIVSGKkNRGFYN
SRK-2      TPKISDFGMARIFgRDETEA      dTRKVVGTGYGMSPEY               AMnGtFSmKSDVFSFGVllEIiSGKRNkGlcd
ARK-1      TPKISDFGMARIFgReETEA      NTRrVVGTGYGMSPEY               AMDGiFSmKSDVFSFGVllLEIiSGKRNkGFYN
ZMPK-1     ePKItDFGlvkllnRggstq      NvshVrGTlGYiaPEw               vssipitaKvDVySyGVvLlElitGtRvselvgg
                  Domain VII              Domain VIII                        Domain IX Cons.                                                                                ------L------                             ------R------
SRK-910    LNHENNLL SYVW   SHWTEGRALEIVDPVIVDSLSSLPATFQPK    EVLKCIQIGLLCVQERAEHRPTMSSVVWML  807
SRK-6      LdyENdLL SYVW   SrWkEGRALEIVDPVIVDSLSSqPsiFQPq    EVLKCIQIGLLCVQELAEHRPaMSSVVWMf
SRK-2      sdsslNLL gcVW   rnWkEGgqLEIVDkVIiD  SSsP TFrPr    EiLrCIQIGLLCVQERvEdRPmMSSVV1ML
ARK-1      sNrdiNLL gfVW   rHWkEGneLEIVDPiniDSLSS  kFpth     EilrCIQIGLLCVQERAEdRPvMSSVmvVL
ZMPK-1     tdevnsmLrklVrmlSaklEGeeqswiDgylLdskLnrpvnyvQar    tliK    lavsCleEdrskRPTMehaVqtl
                                    Domain X                                 Domain XI
```

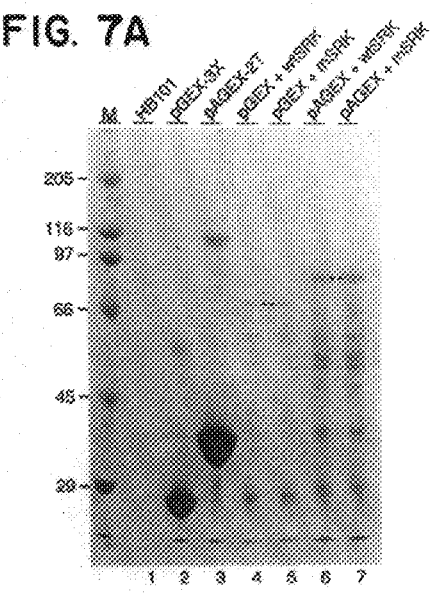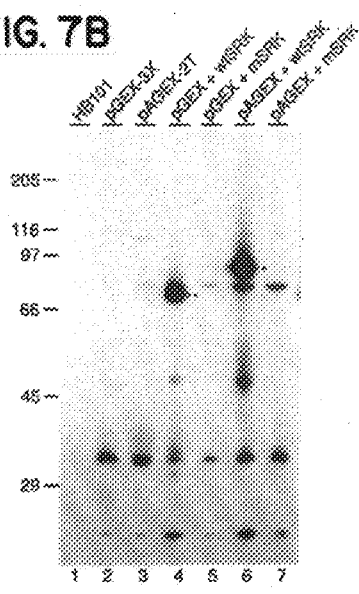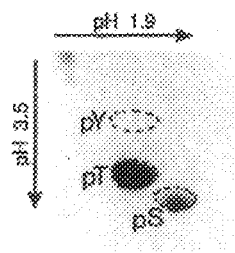

FIG. 9-1

```
Met Lys Gly Val Arg Lys Thr Tyr Asp Ser Ser Tyr Thr Leu Ser Phe
 1               5                  10                 15
Leu Leu Val Phe Phe Val Met Phe Leu Phe His Pro Ala Leu Ser Ile
                20                  25                 30
His Ile Asn Thr Leu Ser Ser Thr Glu Ser Leu Thr Ile Ser Asn Asn
                35                  40                 45
Arg Thr Leu Val Ser Pro Gly Asn Val Phe Glu Leu Gly Phe Phe Arg
 50                                 55                 60
Thr Thr Ser Ser Ser Arg Trp Tyr Leu Gly Ile Trp Tyr Lys Asn Leu
 65                 70                  75                 80
Pro Tyr Lys Thr Tyr Val Trp Val Ala Asn Arg Asp Asn Pro Leu Ser
                85                  90                 95
Asp Ser Ile Gly Thr Leu Lys Ile Ser Asn Met Asn Leu Val Leu Leu
                100                 105                110
Asp His Ser Asn Lys Ser Val Trp Ser Thr Asn Leu Thr Arg Gly Asn
 115                120                 125
```

FIG. 9-2

Glu Arg Ser Pro Val Val Ala Glu Leu Leu Glu Asn Gly Asn Phe Val
130                         135                         140

Ile Arg Tyr Ser Asn Asn Asn Ala Ser Gly Phe Leu Trp Gln Ser
145                         150                         155                    160

Phe Asp Phe Pro Thr Asp Thr Leu Leu Pro Glu Met Lys Leu Gly Tyr
165                         170                         175

Asp Arg Lys Lys Gly Leu Asn Arg Phe Leu Thr Ala Trp Arg Asn Ser
180                         185                         190

Asp Asp Pro Ser Ser Gly Glu Ile Ser Tyr Gln Leu Asp Thr Gln Arg
195                         200                         205

Gly Met Pro Glu Phe Tyr Leu Leu Lys Asn Gly Val Arg Gly Tyr Arg
210                         215                         220

Ser Gly Pro Trp Asn Gly Val Arg Phe Asn Gly Ile Pro Glu Asp Gln
225                         230                         235                    240

Lys Leu Ser Tyr Met Val Tyr Asn Phe Thr Asp Asn Ser Glu Glu Ala
245                         250                         255

FIG. 9-3

```
Ala Tyr Thr Phe Arg Met Thr Asp Lys Ser Ile Tyr Ser Arg Leu Ile
                260                 265                 270
Ile Ser Asn Asp Glu Tyr Leu Ala Arg Leu Thr Phe Thr Pro Thr Ser
            275                 280                 285
Trp Glu Trp Asn Leu Phe Trp Thr Ser Pro Glu Glu Pro Glu Cys Asp
        290                 295                 300
Val Tyr Lys Thr Cys Gly Ser Tyr Ala Tyr Cys Asp Val Asn Thr Ser
    305                 310                 315                 320
Pro Val Cys Asn Cys Ile Gln Gly Phe Lys Pro Phe Asn Met Gln Gln
                325                 330                 335
Trp Glu Leu Arg Val Trp Ala Gly Gly Cys Ile Arg Arg Thr Arg Leu
            340                 345                 350
Ser Cys Asn Gly Asp Gly Phe Thr Arg Met Lys Asn Met Lys Leu Pro
        355                 360                 365
Glu Thr Thr Met Ala Ile Val Asp Arg Ser Ile Gly Arg Lys Glu Cys
    370                 375                 380
Lys Lys Arg Cys Leu Ser Asp Cys Asn Cys Thr Ala Phe Ala Asn Ala
385                 390                 395                 400
```

FIG. 9-4

Asp Ile Arg Asn Gly Gly Ser Gly Cys Val Ile Trp Thr Gly Glu Leu
                405                 410                 415

Glu Asp Ile Arg Asn Tyr Phe Asp Asp Gly Gln Asp Leu Tyr Val Arg
        420                 425                 430

Leu Ala Ala Ala Asp Leu Val Lys Lys Arg Asn Ala Asn Gly Lys Thr
        435                 440                 445

Ile Ala Leu Ile Val Gly Val Cys Val Leu Leu Leu Met Ile Met Phe
    450                 455                 460

Cys Leu Trp Lys Arg Lys Gln Lys Arg Ala Lys Thr Thr Ala Thr Ser
465                 470                 475                 480

Ile Val Asn Arg Gln Arg Asn Gln Asp Leu Met Leu Asn Gly Met Ile
                485                 490                 495

Leu Ser Ser Lys Arg Gln Leu Pro Ile Glu Asn Lys Thr Glu Glu Leu
            500                 505                 510

Glu Leu Pro Leu Ile Glu Leu Glu Ala Val Val Lys Ala Thr Glu Asn
    515                 520                 525

Phe Ser Asn Cys Asn Lys Leu Gly Gln Gly Gly Phe Gly Ile Val Tyr
530                 535                 540

Lys Gly Arg Leu Leu Asp Gly Gln Glu Ile Ala Val Lys Arg Leu Ser
    545                 550                 555                 560

FIG. 9-5

Lys Thr Ser Val Gln Gly Thr Gly Glu Phe Met Asn Glu Val Arg Leu
565                             570                             575

Ile Ala Arg Leu Gln His Ile Asn Leu Val Arg Ile Leu Gly Cys Cys
580                             585                             590

Ile Glu Ala Asp Glu Lys Met Leu Val Tyr Glu Tyr Leu Glu Asn Leu
595                             600                             605

Ser Leu Asp Ser Tyr Leu Phe Gly Asn Lys Arg Ser Ser Thr Leu Asn
610                             615                             620

Trp Lys Asp Arg Phe Asn Ile Thr Asn Gly Val Ala Arg Gly Leu Leu
625                             630                             635                             640

Tyr Leu His Gln Asp Ser Arg Phe Arg Ile Ile His Arg Asp Met Lys
645                             650                             655

Val Ser Asn Ile Leu Leu Asp Lys Asn Met Thr Pro Lys Ile Ser Asp
660                             665                             670

Phe Gly Met Ala Arg Ile Phe Ala Arg Asp Glu Thr Glu Ala Asn Thr
675                             680                             685

Arg Lys Val Val Gly Thr Tyr Gly Tyr Met Ser Pro Glu Tyr Ala Met
690                             695                             700

FIG. 9-6

Asp Gly Val Phe Ser Glu Lys Ser Asp Val Phe Ser Phe Gly Val Ile
705                             710                             715                             720

Val Leu Glu Ile Val Ser Gly Lys Arg Asn Arg Gly Phe Tyr Asn Leu
              725                             730                             735

Asn His Glu Asn Asn Leu Leu Ser Tyr Val Trp Ser His Trp Thr Glu
              740                             745                             750

Gly Arg Ala Leu Glu Ile Val Asp Pro Val Ile Val Asp Ser Leu Ser
              755                             760                             765

Ser Leu Pro Ala Thr Phe Gln Pro Lys Glu Val Leu Lys Cys Ile Gln
              770                             775                             780

Ile Gly Leu Leu Cys Val Gln Glu Arg Ala Glu His Arg Pro Thr Met
              785                             790                             795                             800

Ser Ser Val Val Trp Met Leu Gly Ser Glu Ala Thr Glu Ile Pro Glu
              805                             810                             815

Pro Thr Pro Pro Gly Tyr Ser Leu Gly Arg Ser Pro Tyr Glu Asn Asn
              820                             825                             830

Pro Ser Ser Arg His Cys Asp Asp Glu Ser Trp Thr Val Asn
              835                             840                             845

Gln Tyr Thr Cys Ser Asp Ile Asp Ala Arg
              850                             855

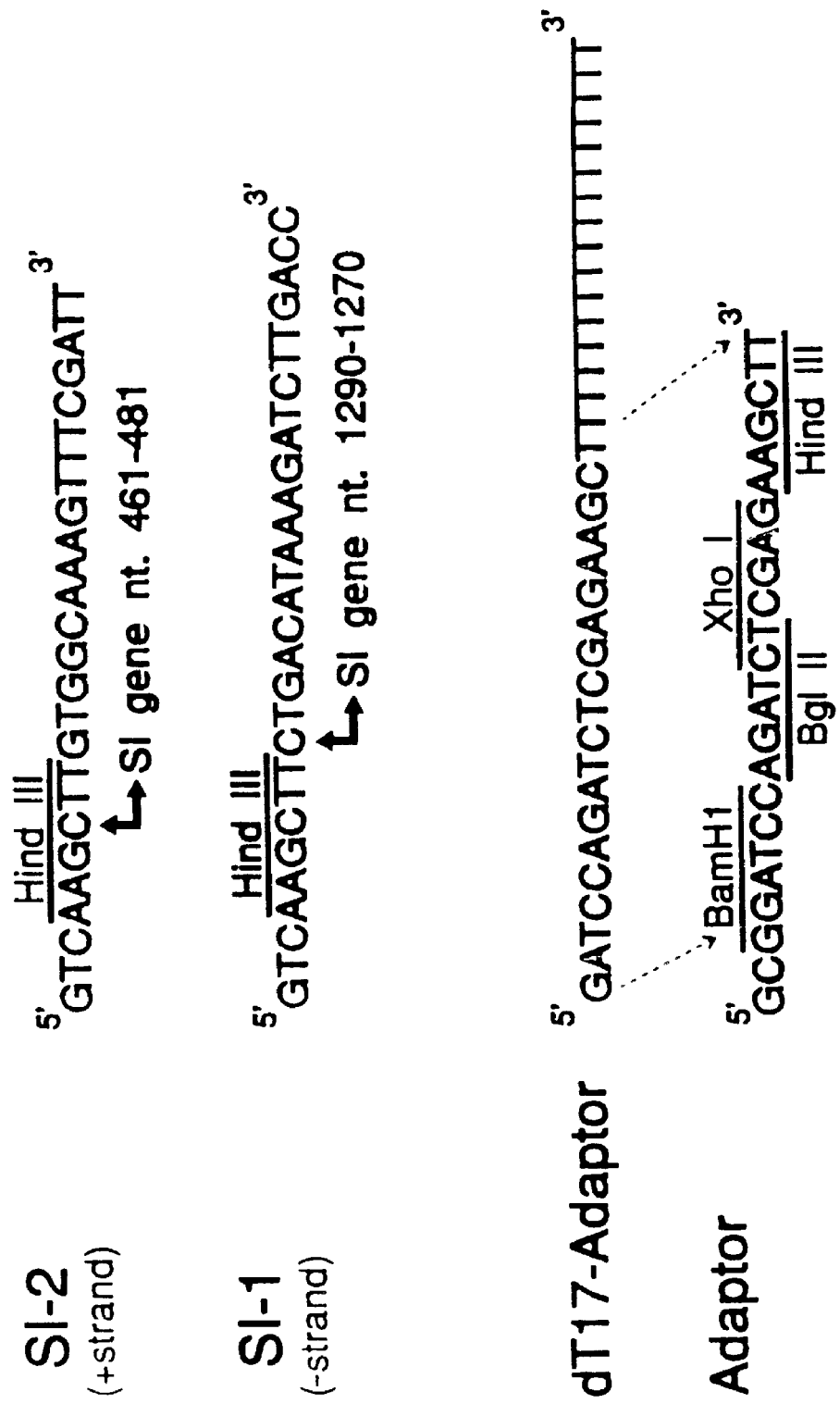

PRIMER 1: 5' AGTAACGATGAGTATTTGGC 3' (+ STRAND)
820 — 839

PRIMER 2: 5' CATATTGAAGGGCTTGAAAC 3' (- STRAND)
1002 — 983

PRIMER 3: 5' TCCGGAATTACTTTGATGAC 3' (+ STRAND)
1256 — 1275

PRIMER 4: 5' GAAAGGTTGCTGGTAATGAT 3' (- STRAND)
2323 — 2304

S-LOCUS RECEPTOR KINASE GENE IN A SELF-INCOMPATIBLE BRASSICA NAPUS LINE

This application is a continuation of application Ser. No. 07/959,945, filed Oct. 8, 1992, now abandoned, which is a CIP of application Ser. No. 07/847,564, filed on Mar. 3, 1992, now abandoned.

BACKGROUND OF THE INVENTION a. Field of the Invention

The present invention is directed to an isolated gene from the S-locus of Brassica, i.e., the S-locus receptor kinase 910 (SRK-910) gene. More particularly, the present invention is directed to an isolated cDNA sequence which encodes for the SRK-910 protein. The presence of the SRK-910 gene at the S-locus of Brassica is associated with expression of the self-incompatibility (SI) phenotype. The present invention is also directed to the recombinant SRK-910 protein. The present invention is further directed to specific cDNA probes that are capable of hybridizing with the SRK-910 gene and the isolated cDNA sequence. The present invention is useful because it permits the rapid identified of Brassica progeny that manifest the self-incompatibility (SI) phenotype.

b. Background of the Invention

Self-incompatibility is an interesting example of cell-cell recognition in plants. There are at least fifty different alleles in Brassica and in each case the stigma papillae cells must be able to differentiate between self-pollen and pollen derived from parents carrying different S-alleles. Once this recognition event occurs, it sets in motion a train of physiological events that prevents the germination of self-incompatible pollen, while allowing the germination and subsequent fertilization by self-compatible pollen even when both types are present on the stigma surface (Gaude and Dumas, 1987).

In animal cells, this type of recognition event is often mediated by plasma membrane-associated receptor kinases (Cadena & Gill, 1992). In these cases, the receptor binds to the extracellular ligand molecule and the binding stimulates a change in conformation of the kinase domain thereby stimulating kinase activity which regulates the subsequent changes in gene expression (Cantley et al., 1991; Karen, 1992). In plants, much less is known about this type of signal recognition process in general, and in the self-incompatibility response in particular.

Signal transduction by receptor kinases occurs in many aspects of cell growth, development and differentiation (Karin, 1992; Cadena & Gill, 1992). The majority of receptor kinases characterized to date have been found to specifically phosphorylate tyrosine residues (Ullrich & Schlessinger, 1990). Mutations in these types of receptors have also been implicated in oncogenesis (Aaronson, 1991; Cantley et al. 1991). Recently, there have been a few reports of other receptor kinases with homologies to serine/threonine cytoplasmic kinases. One of these receptor kinases has been shown to possess serine/threonine phosphorylation activity (Lin et al., 1992), while another displays serine, threonine and tyrosine kinase activity (Douville et al., 1992). In plants, there is very little known about the role of receptor kinases in signal transduction. There have been three reports on the isolation of plant receptor kinases (Walker & Zhang, 1990; Stein et al., 1991; Tobias et al., 1992). Based on sequence homology only, these genes appear to encode serine/threonine kinases. One of these receptor kinases, SRK-6, has been implicated in the self-incompatibility system of Brassica oleracea (Stein et al., 1991).

Self-incompatibility in Brassica is controlled by a single dominant genetic locus called the S-locus (Bateman, 1955). The sporophytic nature of this incompatibility system results in the pollen phenotype being derived from the genotype of the diploid pollen parent and not from the haploid pollen genotype. This is hypothesized to occur by the deposition of an S-factor in the exine (outer coat) of the pollen grain by the anther tapetum (parental tissue) during pollen development (de Nettancourt, 1977). When a pollen grain lands on the stigma surface, the action of the S-locus results in a block in fertilization if the same S-allele is present in the pollen parent and the pistil. The response is very rapid, and for the stronger alleles, leads to a block in pollen hydration or some hydration and germination, and an inability to penetrate the stigma barrier (Zuberi & Dickinson, 1985); Gaude & Dumas, 1987). There are multiple alleles at the S-locus and it has ben estimated that in B. oleracea there are nearly 50 different alleles (Ockendon 1974, 1982). In heterozygous plants, the majority of B. oleracea S-alleles have been found to be dominant, codominant, or recessive to the second allele in a non-linear arrangement dependent on the allele combinations. A few alleles, called pollen recessive alleles, have been shown to be always recessive to other S-alleles in the pollen (Thompson & Taylor, 1966). Both of the diploid Brassica species, B. campestris and B. oleracea, possess this self-incompatibility system, while B, napus an allotetraploid composed of the B. campestris and B. oleracea genomes, generally occurs as a self-compatible plant (Downey & Rakow, 1987). There are a few naturally occurring self-incompatible B. napus lines (Olsson, 1960, Gowers, 1981), and self-incompatible lines have also been generated by introgressing an S-locus from B. campestris (Mackay, 1977).

Initial studies on the Brassica self-incompatibility system have shown that there is an abundant soluble glycoprotein present in the cell wall of the stigma papillae cells associated with this response (Nasrallah et al., 1970; Hinata & Nishio, 1978; Kandasamy et al., 1989). Several genes for these S-locus glycoproteins ("SLG") have been cloned and characterized (Nasrallah et al., 1987; Trick & Flavell, 1989; Dwyer et al., 1991). Among the alleles associated with a strong incompatibility phenotype, there is greater than 80% homology at the DNA level (Dwyer et al., 1991). The weak pollen recessive alleles are also highly homologous to each other, but only about 70% homologous to the first group of phenotypically strong alleles (Scutt & Croy, 1992). Transformation of a self-compatible B. napus line with these SLG alleles does not produce a self-incompatibility phenotype (Nishio et al., 1992). Recently, a second gene at the S-locus has been cloned from B. oleracea. This second gene, a S-locus receptor kinase gene (SRK-6), shows sequence homologies at its N-terminal end to SLG genes and at its C-terminal end to serine/threonine kinases (Stein et al., 1991).

It is an object of the present invention to find and isolate one or more genes that are associated with the self-incompatibility phenotype of Brassica. It is a further object of the present invention to characterize the isolated gene and to develop probes that would enable one to rapidly screen the progeny of cross fertilizations between Brassica species for the self-incompatibility (SI) phenotype.

SUMMARY OF THE INVENTION

The present invention has multiple aspects. In its first aspect, it is directed to an isolated gene, the SRK-910 gene, from the S-locus of Brassica. The presence of the SRK-910 gene at the S-locus of Brassica is associated with the presence of the self-incompatibility (SI) phenotype in that species. In its second aspect, the present invention is directed to an isolated cDNA (SEQ ID No. 1) that corresponds to an allele of the self-incompatibility locus (SI-locus) of Brassica. The isolated cDNA (SEQ ID No. 1) has 2749 nucleotides and the sequence in FIG. 4. The isolated cDNA encodes for the S-locus receptor kinase-910 protein ("the SRK-910 protein"), which plays a role in the self-incompatibility of Brassica. The number "910" refers to the 910 gene, which in our parent application U.S. Ser. No. 07/847,564, was established to segregate with the W1 SI phenotype. The SRK-910 protein (SEQ ID No. 2) has 858 amino acids (FIG. 9) and is encoded for by the first 2574 nucleotides of the isolated cDNA (SEQ ID No. 1) of the present invention.

The present invention is also directed to a DNA probe that is capable of hybridizing within the nucleotide sequence of FIG. 4 but not with the nucleotide sequences of partially homologous genes at the S-locus that encoding for the SLG glycoproteins. The DNA probe of the present invention is a member of a group of four oligonucleotide probes, as shown in FIG. 12 herein and having SEQ ID Nos. 5–8.

In another aspect, the present invention is directed to a vector comprising the isolated cDNA (SEQ ID No. 1) of the present invention. Preferably, the vector further comprises the isolated cDNA corresponding to the SLG-910 allele which is taught in our parent application (U.S. Ser. No. 07/847,564) which is incorporated herein by reference. Most preferably, the vector is a transfer vector.

In yet another aspect, the present invention is directed to a method for conferring the self-incompatible (SI) phenotype on a self-compatible (SC) plant. The method comprises transferring the transfer vector of the present invention into a self-compatible plant, plant tissue or plant protoplast that is capable of assimilating the transfer vector and expressing self-incompatibility.

BRIEF DESCRIPTION OF THE FIGURES

FIG. 3 is a blot of genomic DNA taken from F2 plants derived from a cross between an SI plant homologous for W1 (Lane 1) and an SC plant homologous for Westar (Lane 3) to produce a heterologous W1 X Wester F1 (Lane 2) which was then self pollinated to produce an F2 population (Lanes 4–19). The genomic DNA was digested with Hind III and hybridized to the entire SRK-910 coding region. The plants in Lanes 1, 2 and 4–11 are self-incompatible (SI) while the plants in Lanes 3 and 12–19 are self-compatible (SC).

FIG. 4 is the nucleotide sequence and predicted amino acid sequence of the SRK-910 gene (SEQ ID No. 1). The underlined sections represent the signal peptide and trans-membrane domain, respectively. Conserved cystein residues are marked by a dash above the amino acid residue. Potential N-glycosylation sites are represented by bold-italic type. The nucleotide sequence has been submitted to GenBank, IntelliGenetics, Inc., Mountain View, Calif., Accession No. M97667.

FIG. 6 represents an alignment of kinase domains from plant receptor kinases. Using conventional single letter designations (Table 1) for amino acids, the amino acid sequence of the SRK-910 kinase domain is compared to that of SRK-6 and SRK-2 from *B. oleracea* (Stein et al., 1991), ARK-1 from Arabidodpsis (Tobias et al., 1992); and ZMPK-1 from corn (Walker & Zhang, 1990). Capital letters indicate amino acids that are the same as the SRK-910 protein while differences are denoted by small letters. As defined by Hanks et al. (1988), the kinase sequences have been divided into 11 domains. The amino acids that are conserved in protein kinases are shown in the top line. The bold type represents amino acid that are absolutely conserved and the regular type represents conserved amino acid groups as defined by Hanks et al. (1988). The two underlined regions represent consensus sequences found in serine/threonine kinases.

FIG. 7 is an analysis of SRK-910 kinase activity in *E. coli*. FIGS. 7A and 7B represent SDS-PAGE gel containing glutathione S-transferase ("GST") fusion proteins extracted with glutathione agarose beads and tested for kinase activity (autophosphorylation) by the addition of $\gamma^{32}P$-ATP. A coomassie blue stain of the gel is shown in A and an autoradiogram to detect phosphorylated proteins is shown in B. Sigma brand SDS molecular weight markers (M) are shown on the left. In both FIGS. 7A and 7B, the lanes are as follows: Lane 1: HB101 extract with no plasmids; Lanes 2 and 3: control plasmids without an SRK-910 insert; Lanes 4 and 6: wt SRK-910 kinase domain fused to the two different vectors; Lanes 5 and 7: SRK-910 kinase domain carrying a mutated lysine fused to the two different vectors. The full length fusion proteins are marked by dots.

FIG. 7C is a phosphoamino acid analysis of the "protein A- GAST-(SRK-910) receptor kinase" ("AGST-kinase") fusion protein. Hydrolysed amino acids were separated by two-dimensional thin-layer electrophoresis. The positions of the control phosphoamino acids visualized by ninhydrin are marked by the dotted circles. pY=phosphotyrosine, pT=phosphothreonine, pS=phosphoserine.

FIG. 9 is the amino acid sequence of the SRK-910 protein using one letter symbols (Table 1).

FIG. 10 illustrates the general self-incompatibility primers used in the isolation of the SRK-910 cDNA. SI-1 (SEQ ID No. 4) and SI-2 (SEQ ID No. 3) represent conserved regions shown in published SLG sequences. Primers were made from these sequences and used in the PCR reaction to amplify the W1 associated bands from genomic DNA. The adaptor (SEQ ID No. 10) and $dT_{17}$-adaptor (SEQ ID No. 9) primers were designed according to Frohman et al. (Proc. Natl. Acad. Sci. 85:8998–9002, 1988), with different restriction enzyme sites incorporated into the adaptor primer.

DETAILED DESCRIPTION OF THE INVENTION

Figure 1:
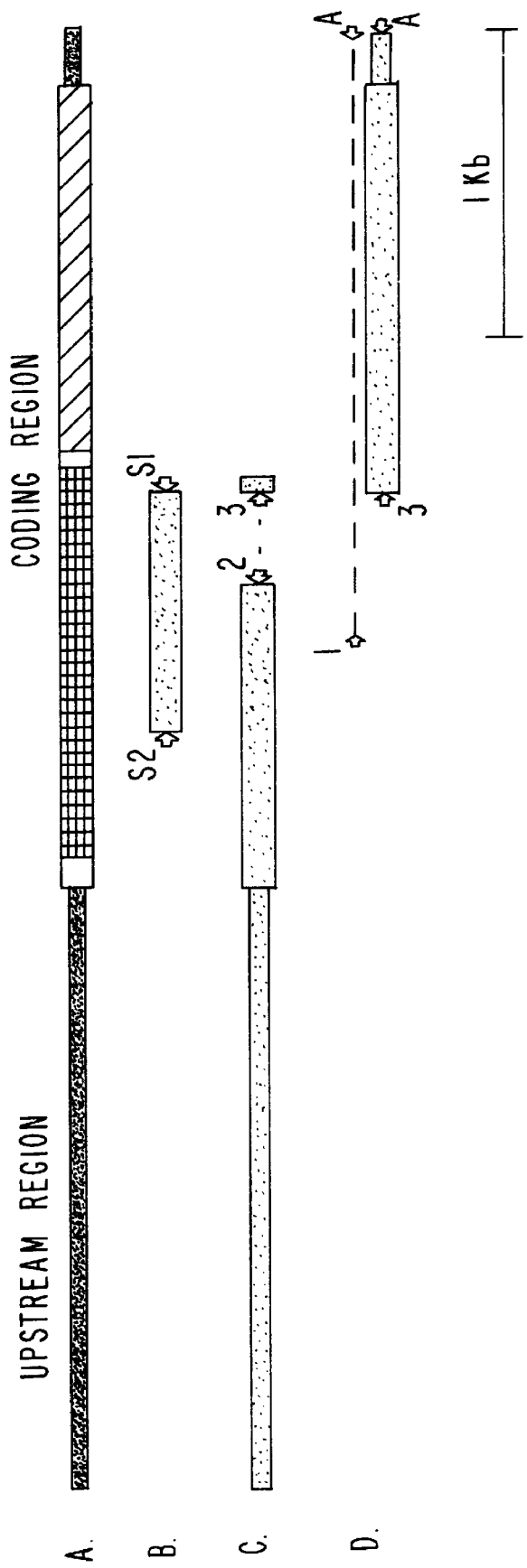
FIG. 1A is a composite of the regions cloned from the SRK-910 gene. The dotted portion of the Coding Region represents the receptor domain. The cross hatched portion of the Coding Region represents the kinase domain.
FIG. 1B is a 800 bp genomic fragment of the SRK-910 gene isolated from the SLG-homology domain using the general self-incompatibility primers SI-1 (SEQ ID No. 4) and SI-2 (SEQ ID No. 5), both of FIG. 10.
FIG. 1C is a genomic fragment encompassing the 5' end isolated by inverse PCR using the SRK-910 specific primers: primer 2 (SEQ ID No. 6) and primer 3 (SEQ ID No. 7), both of FIG. 12.
FIG. 1D is a CDNA clone composed of the 3' end isolated by 3' RACE using the SRK-910 specific primers: primer 1 (SEQ ID No. 5) and primer 3 (SEQ ID No. 7), both of FIG. 12.

The present invention is directed to an isolated gene, the SRK-910 gene, which was isolated from the SI locus of the self-incompatible canola line, *Brassica napus* ssp. *oleifera* W1. The S-locus in the W1 line gives a very strong self-incompatibility response and provides a useful line and S-allele for producing hybrid canola lines that exhibit self-incompatibility.

In its second aspect, the present invention is directed to an isolated cDNA i.e., the cDNA (SEQ ID No. 1) of FIG. 4 having 2749 nucleotides. The cDNA of the present invention (SEQ ID No. 1) was isolated from the self-incompatible canola line (*Brassica napus* ssp. *oleifera*) W1 which was produced by introgressing a *B. campestris* S-locus into the self-compatible Westar canola cultivar.

The present invention is further directed to nucleotides 1–2574 of the isolated cDNA which encode for the S-locus receptor kinase 910 protein ("the SRK-910 protein"). The SRK-910 protein (SEQ ID No. 2) comprises the sequence of 858 aminoacids of FIG. 9.

The preparation of the W1 line is fully described in our copending U.S. patent application Ser. No. 07/847,564, which is incorporated herein by reference. By way of summary, WI is a self-incompatible *B. napus* ssp. *oleifera* (canola) cultivar derived from the introgression of a *B. campestris* S-locus into the self-compatible (SC) canola Westar line. DNA blot analysis of W1 genomic DNA with the SLG-A14 allele isolated from another canola line (U.S. Ser. No. 07/847,564) revealed two cross-hybridizing Hind III bands of 3.6 kb and 6.5 kb, respectively. A gene corresponding to the 6.5 kb band was isolated and characterized in our parent application (U.S. Ser. No. 07/847,564). The gene that was isolated from the 6.5 kb band was found to encode for a highly expressed SLG-910 allele which segregates with W1 self-incompatibility.

The present invention, which is a continuation of the work in U.S. Ser. No. 07/847,564 is directed to our isolation and cloning of a different gene, the S-locus receptor kinase (SRK) 910 gene from the above mentioned 3.6 kb band. In the present invention, we have determined that the SRK-910 gene also segregates with W1 self-incompatibility.

MATERIALS AND METHODS

Standard chemical materials and standard molecular biological methods were used in this invention. Modifications to the protocols were made as described herein.

Genomic DNA Extraction

Genomic DNA was extracted from leaves using a modified version of Fedoroff et al. (Genet. 2:11–29, 1983.) Approximately 1 g of tissue was homogenized in a mortar and pestle in the presence of liquid nitrogen. Six milliliters (mls) of extraction buffer (8M urea, 350 mM NaCl, 50 mM Tris-Cl, pH 7.5, 20 mM EDTA, 2% Sarcosine) were added to the tissue and grinding was continued until the materials were thawed. The mixture was then transferred to an 15 ml polypropylene tube, and 0.6 ml 10% SDS and 6 ml phenol/chloroform/isoamyl-alcohol (75:24:1) were added. The mixture was gently shaken for 10 min. and separated by centrifugation. The supernatant was then extracted with 1 volume of phenol/chloroform/isoamyl-alcohol (25:24:1) followed by an extraction with chloroform/isoamyl-alcohol (24:1). The nucleic acids were precipitated with a ¹⁄₁₀th volume of 3M sodium acetate and 2 volumes ice-cold ethanol. Nucleic acid was then resuspended in 2 ml 10 mM Tris-Cl, pH 8.0, 45 mM EDTA and treated with 60 μg RNAse A at 37° C. for 30 min. The DNA was ethanol-precipitated and resuspended in 100–200 μl TE (10 mM Tris, 1 mM EDTA, pH 7.5). A scaled down version which involved grinding one leaf in an eppendorf tube was utilized for the F2 plants. For the purpose of rapidly screening seedlings for the presence of S-alleles, DNA was prepared by the method of Edwards and Thompson, (Nucl. Acids. Res. 19:1349, 1991).

Genomic DNA Blots

Approximately 5 to 10 μg of genomic DNA was digested to completion with the restriction endonuclease Hind III (Bethesda Research Laboratories, Bethesda, Md.). Digested DNA was then fractionated through a 0.7% agarose gel, and transferred to a Zetabind™ membrane (Cuno Labs Inc., Meridien, Conn.) by blotting in 20× SSC (20× SSC=3M sodium acetate, 0.3M $Na_3$ citrate. $2H_2O$. After drying, the membrane was prewashed in 0.1× SSC, 0.5% sodium dodecylsulfate solution (SDS) for 30 min. at 60° C. The membranes were prehybridized at 42° C. in 5× SSPE, 10× Denhardt's (10× Denhardt's=1 g Ficoll 400, 1 g polyvinylpyrrolidone, 1 g bovine serum albumin [Pentax fraction V], in 500 ml of distilled water), 0.5% SDS for approximately one hour, hybridized overnight at 42° C. in 50% formamide, 10% dextran sulfate, 5× SSPE, 0.5% SDS, and 50 μg/μl sheared salmon sperm DNA. Filters were then washed at 68° C. to 70° C. in 0.1× SSC, 0.1% SDS. Hybridization probes consisting of full length cDNAs were digested with the appropriate restriction endonucleases to excise the cDNA from the vector. The excised cDNA was separated from the vector by electrophoresis on an agarose gel. Probes were labelled by random-priming using the method of Feinberg & Vogelstein, (Anal. Biochem. 132:6–13, 1983.)

DNA Sequencing

The 5' and 3' cDNA end clones were partially sequenced using dideoxy sequencing method of Sanger and the Sequenase enzyme (United States Biochemicals, Cleveland Ohio) (Sanger, F., et al., Proc. Natl. Acad. Sci. U.S.A. 74:5463–5467). To sequence the full length cDNA clones, deletions were made using exonuclease III and Mung Bean nuclease according to the procedure in the Stratagene kit (Stratagene, LaJolla, Calif.). Overlapping deletions were sequenced for both strands. All DNA and protein sequence analysis was performed on the DNASIS and PROSIS software. (Pharmacia, Piscataway, N.J.).

RNA extraction

Total RNA was extracted from about 100–200 mg of tissue using the method of Jones et al. (EMBO J. 4:2411–2418, 1985.) 10 to 30 μg of RNA was fractionated through a 1.2% formaldehyde-agarose gel (Sambrook et al., A Laboratory Manual. 2nd ed. Cold Spring Harbor Laboratory Press, 1989) and transferred to Zetabind™ membrane (Cuno Labs. Inc.) in 20× SSC. Hybridization and washing conditions were the same as used for the genomic blots.

DESCRIPTION
Isolation Of The SRK-910 Gene In The W1 Line

Figure 11:
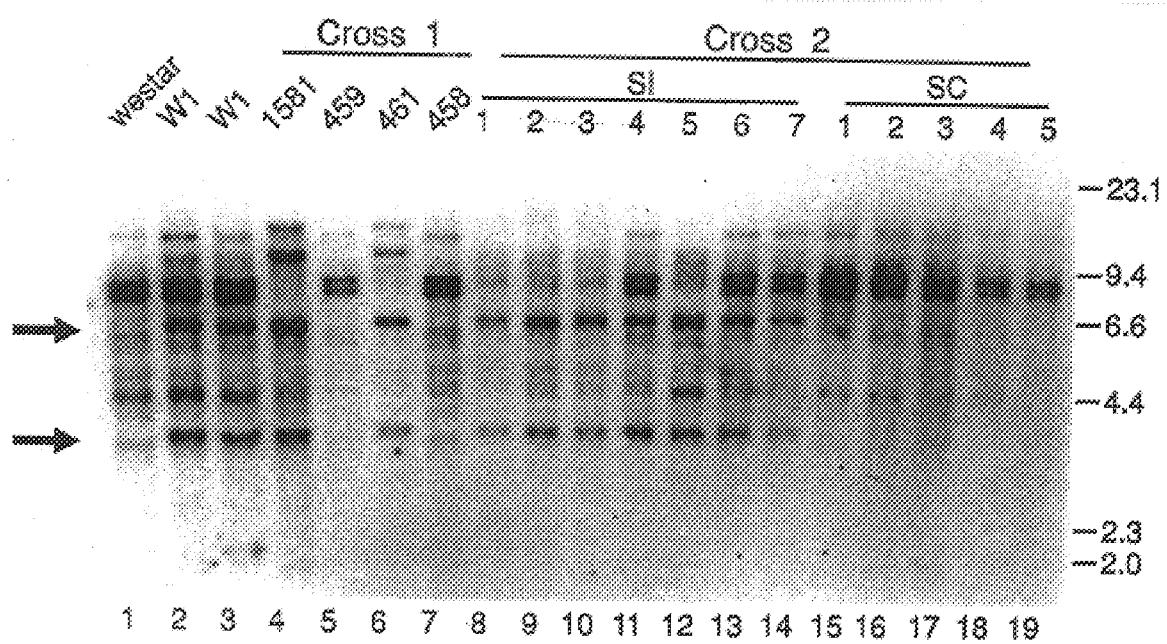
FIG. 11 illustrates a genomic DNA blot analysis of related SLG sequences. Genomic DNA samples were digested with Hind III, hybridized with the A14 CDNA and washed at reduced stringency to detect cross hybridizing genes. The genomic DNA samples are the SC Westar (Lane 1), SI W1 (Lanes 2 and 3), and progeny from two different 3-way crosses involving W1 and various SC canola lines. Lanes 3–6 represent one cross, and Lanes 7–19 represent the second cross. The plants were tested for self-incompatibility by seed set. Lanes 4, 6 and 8–14 are SI, and Lanes 5, 7 and 15–19 are SC. The arrows mark two cross-hybridizing bands which are only present in the genomic DNA samples from SI plants.

The initial characterization of the W1 line involved hybridization of the A14 cDNA as described in Example 1 of U.S. Ser. No. 07/847,564 to a genomic DNA blot washed with reduced stringency at 50° C. in 1×SSC 0.1% sodium dodecyl sulfate (SDS), which allows hybridization to sequences having about 65% homology and greater. Under these conditions, multiple bands could be detected in both SI and SC plants as illustrated (FIG. 11). However, two hybridizing bands were found to be present in W1 genomic DNA (FIG. 11, Lanes 2 and 3) and in SI plants (FIG. 11, Lanes 4, 6, 8–14) derived from two different crosses involving W1. The SC Westar line (FIG. 11, Lane 1) and SC progeny (FIG. 11, Lanes 5, 7 and 15–19) from the crosses did not contain these fragments.

To isolate the W1 associated fragments, oligomers for PCR amplification were designed to highly conserved regions in published SLG sequences as illustrated in FIG. 10. The SI-2 (+)-strand primer (SEQ ID NO: 3) corresponds to nucleotides 461–481 of the conserved region of the A14 cDNA and SI-1 (−) strand primer (SEQ ID NO: 4) corresponds to a sequence complimentary to nucleotides 1290–1270 of the conserved region of the A14 cDNA. PCR amplification was performed according to a modification of the method described by Saiki et al. (Science 230:1350, 1985). Two different sources of DNA were used; the W1 homozygote (FIG. 11, Lane 2) and the 1581 plant (FIG. 11, Lane 4). W1 and 1581 genomic DNA were digested with Hind III and fractionated on a 0.7% agarose gel. The regions in the gel spanning 3.6 to 3.9 kb and 6.5 to 6.9 kb were excised and the DNA was isolated by electroelution. Approximately 50 ng of the fractionated genomic DNA was used in a 100 μl PCR reaction with 1 μM of each primer, SI-1 (SEQ ID No. 4) and SI-2 (SEQ ID No. 3), 200 μM each dNTP, and 2.5 units of Taq polymerase. The PCR conditions were 94° C. for 1.5 min., 45° C. for 1 min., and 72° C. for 1.5 min. for a total of 30 cycles. The PCR products were cloned into pBluescript (Stratagene, LaJolla, Calif.) by standard methods. The expected product size was roughly 800 bp starting approximately 400 bp from the 5' end. The cloned PCR products were partially sequenced as described in U.S. Ser. No. 07/847,564 to determine their identity, and then used as probes on genomic blots. From the 6.5 kb region, two different clones were obtained. One clone was specific for the 1581 plant. The second clone, 910, hybridized to the upper W1 specific band (FIG. 11).

Figure 12:
FIG. 12 provides the nucleotide sequence and location for the SRK-910 specific primers, namely "primer 1" (SEQ ID No. 5), "primer 2" (SEQ ID No. 6), "primer 3" (SEQ ID No. 7), and "primer 4" (SEQ ID No. 8). The primers were chosen by comparing the partial SRK-910 genomic sequence to published SLG and SRK sequences and selecting the variable regions. Compare for example FIG. 6.

From the 3.6 kb region, only one PCR clone, 1631, having about 800 bp was obtained and it was found to hybridize to the lower W1 specific band (FIG. 3). (An RNA blot analysis, which was performed (not shown), revealed that only a single gene was highly expressed in the stigma. That single gene was further characterized as described below.) The sequence analysis of the 800 bp genomic PCR clone (FIG. 1B) showed high levels of homology (89%) to the SLG-910 gene. Notwithstanding the high degree of homology, we produced three specific primers from this 800 bp region that were designed to isolate the remainder of the coding region for the novel gene (now designated as SRK-910). The three specific primers are referred to herein as "primer 1" (SEQ ID No. 5), "primer 2" (SEQ ID No. 6), and "primer 3" (SEQ ID No. 7). As shown in FIG. 12, primer 1 is a (+) strand primer (SEQ ID No. 5) corresponding to nucleotides 820 to 839 of the SRK-910 gene; primer 2 is a (−) strand primer (SEQ ID No. 6) corresponding to a sequence complementary to nucleotides 1002 to 983 of the SRK-910 gene; and primer 3 is a (+) strand (SEQ ID No. 7) corresponding to nucleotides 1256 to 1275 of the SRK-910 gene.

The 5' end of the SRK-910 gene was amplified using the inverse PCR technique (Ochman et al., 1988). Hind III digested W1 genomic DNA from the 3.6 kb region was extracted, circularized by ligation, and amplified with primers 2 and 3 (SEQ ID Nos. 6 and 7 respectively). Primers 2 and 3 were oriented in opposite directions (FIG. 1C). Sequence analysis revealed that the inverse PCR fragment contained 59 bp at the 3' end of the SLG homology region plus approximately 400 bp of an intron following this region. At the 5' end, 1 kb of the coding region with no introns, and another 1.8 kb upstream of the initiation codon was present.

The 3' end of the SRK-910 gene was isolated by amplification of pistil cDNA using the RACE procedure (Frohman et al., 1988) with two sequential rounds of amplification utilizing primers 1 and 3 (SEQ ID Nos. 5 and 7 respectively). This PCR cDNA fragment was 1.5 kb in length starting at the 3' end of the SLG homology region (FIG. 1D).

The sequence of the SRK-910 coding regions was derived from the three overlapping clones in FIG. 1B–D. For the 3' end, three different PCR cDNA clones were sequenced and found to have small insertions or deletions which were not present in the other clones. Stein et al. (1991) found that another gene, a B. oleracea SRK gene, contained a large intron following the SLG homology region followed by 5 small introns in the remainder of the 3' end. In the present invention, the changes that were observed corresponded to the location of some of these introns, yet each cDNA clone had a different alteration suggesting that the changes were due to splicing errors. Clone 26 contained a 88 bp insert at the site of the 4th intron. Clone 24 had a 5 bp deletion at the 3rd intron splice site. The last clone, clone 10, contained a 41 bp deletion by the 4th intron and a 20 bp insert at the 5th intron. Since the alterations in each of these clones were different, a correct cDNA could be constructed using clones 24 and 26.

Figure 2:
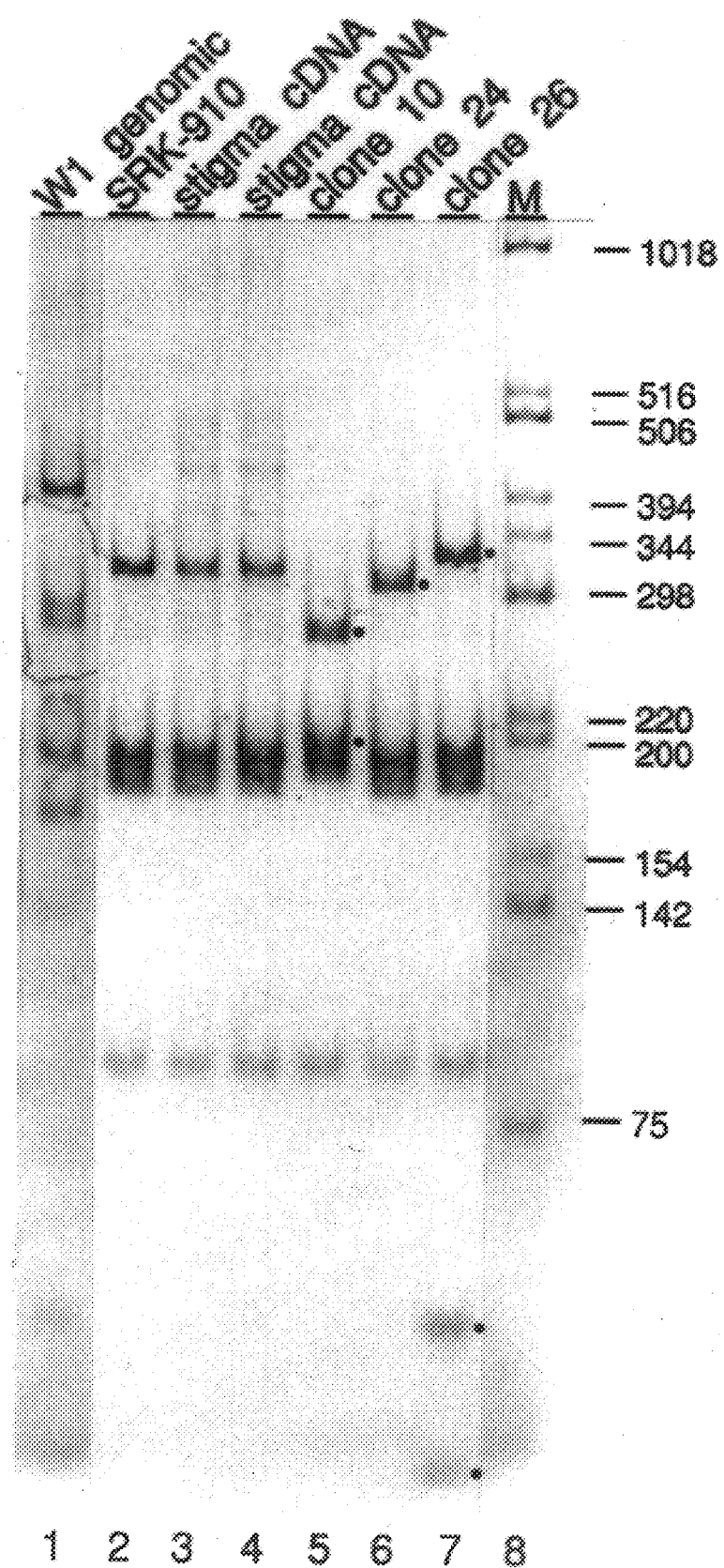
FIG. 2 is an analysis of the SRK-910 message for intron splicing. The kinase domain was amplified from various samples and digested with Alu I to look for the presence of introns. Sources of DNA for PCR amplification are as follows: Lane 1: W1 genomic DNA; Lane 2: a reconstructed SRK-910 clone carrying the correct coding region; Lanes 3 and 4: amplified CDNA directly from stigma cDNA; Lanes 5–7: altered SRK-910 cDNA clones 10, 24, and 26; Lane 8: 1 kb ladder (BRL). The altered Alu 1 fragments in the cDNA clones are marked by dots (Lanes 5–7).

To determine if the SRK-910 gene was frequently processed incorrectly or if a cloning problem led to the isolation of altered cDNAs, cDNA PCR products were analyzed before the cloning stage. Using primers outside of the 5 small introns (nucleotides 1378-2323), stigma cDNA, genomic DNA, and the three altered cDNA clones were amplified. (FIG. 2). For the stigma cDNA PCR products, a clear band was detected, in addition to a faint smear of slightly larger molecular weight products (not shown). The PCR products were digested with Alu I which produces 5 small fragments (298, 197, 183, 175, and 91 bp) for the correct cDNA clone (FIG. 2, Lane 2). The PCR products from the directly amplified stigma CDNA samples showed the same digest patterns (FIG. 2, Lanes 3 and 4) as the correct cDNA clone. The PCR products from the altered cDNA clones show some differences (FIG. 2, Lanes 5–6, marked by dots). The insertion in clone 26 contained two Alu I sites producing two small bands (47 and 30 bp; FIG. 2, Lane 7) which are also present in the genomic sample (FIG. 2, Lane 1) confirming that the insert originates from the gene. Thus, the majority of the SRK-910 message is processed correctly.

Segregation of the SRK-910 Gene With Self-Incompatibility in the W1 Line

During the initial analysis of the W1 S-locus, it became apparent that there were other related genes in the W1 genome, such as non-functional S-loci present in the original self-compatible Westar line, and distinct loci which share homology to the S-locus (see Lalonde et al., 1989; Boyes et al., 1991; and U.S. Ser. No. 07/847,564). Thus, it was important to confirm that the isolated SRK-910 gene is associated with W1 self-incompatibility. A segregating $F_2$ population was produced by crossing a homozygous self-compatible Westar plant. The heterozygous $F_1$ plants were self-pollinated to produce a $F_2$ population of W1 /W1 , W1 /Westar, and Westar/Westar plants. These plants were then tested for self-incompatibility by self-pollination, and reciprocal crosses to the W1 and Westar parental lines (U.S. Ser. No. 07/847,564). In addition, genomic DNA samples from these plants were hybridized to the 2.8 kb SRK-910 coding region to determine if this gene segregated with W1 self-incompatibility (FIG. 3).

TABLE 1

ABBREVIATIONS FOR AMINO ACIDS

| Amino Acid | Three-Letter Abbreviations | One-Letter Symbol |
|---|---|---|
| Alanine | Ala | A |
| Arginine | Arg | R |
| Asparagine | Asn | N |
| Aspartic Acid | Asp | D |
| Asparagine or aspartic acid | Asx | B |
| Cysteine | Cys | C |
| Glutamine | Gln | Q |
| Glutamic Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The SRK-910 clone was found to hybridize to two Hind III fragments only in DNA samples extracted from plants displaying the W1 self-incompatibility phenotype (FIG. 3, Lanes 1, 2 and 4–11). Accordingly, the SRK-910 gene represents a second gene at the W1 S-locus that segregates with self-incompatibility. (In our parent application (U.S. Ser. No. 07/847,564), we established that SLG-910 gene at the W1 S-locus also segregated with self-incompatibility).

Sequence Analysis of the SRK-910 Gene

Figure 5:
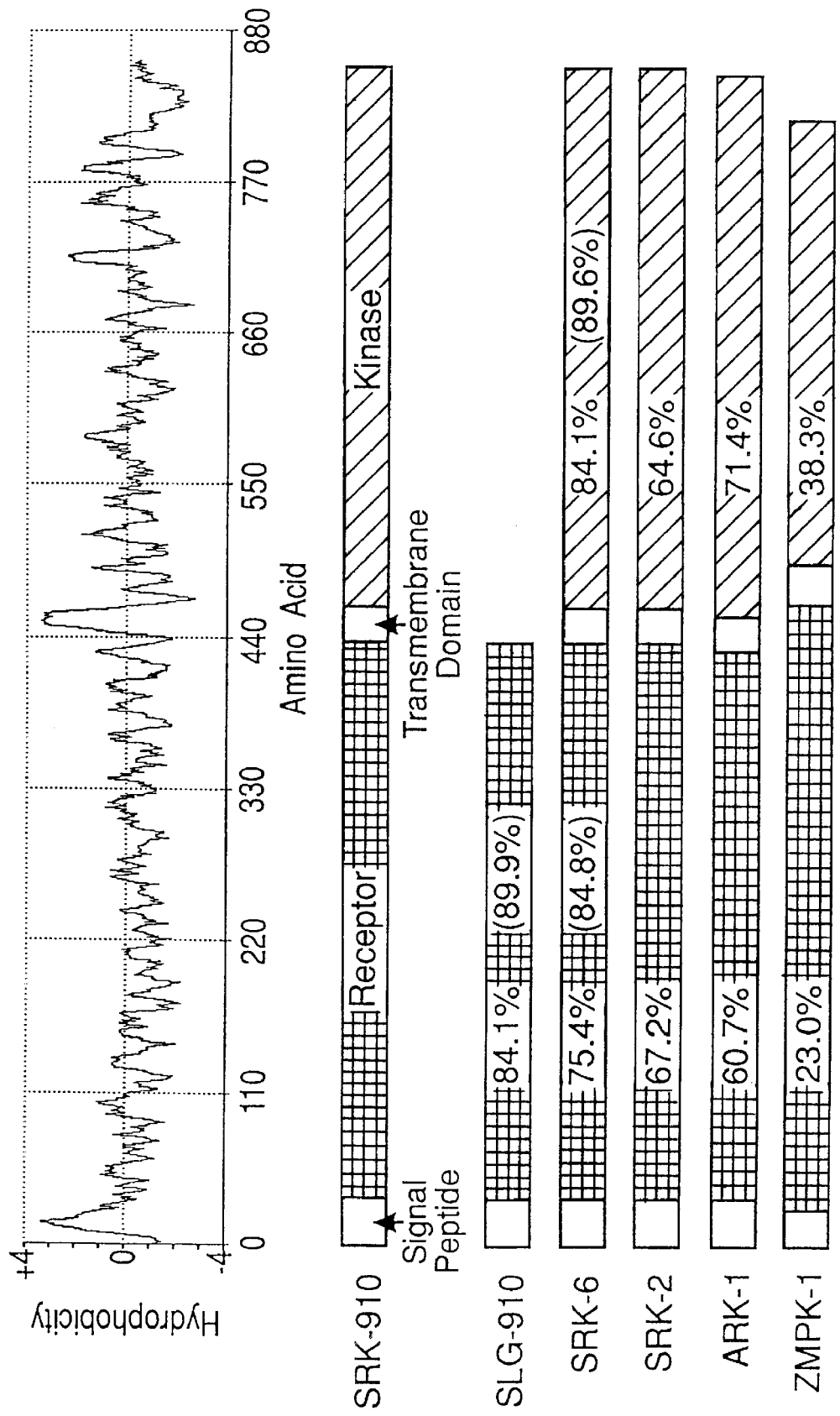
FIG. 5 is an analysis of the SRK-910 sequence. At the top of the figure, there is a Kyte hydropathy plot of the predicted amino acid sequence generated by PROSIS software (using a window value of 10). Increased hydrophobicity is indicated by positive values. Below the plot, the domains of the SRK-910 protein are illustrated and compared. A comparison of amino acid homology is shown between the SRK-910 receptor and its SLG-910 counterpart. The SRK-910 receptor and kinase domains are also compared to SRK-6 and SRK-2 from *B. oleracea* (Stein et al., 1991), to ARK-1 from Arabidopsis (Tobias et al., 1992); and to ZMPK-1 from corn (Walker & Zhang, 1990). DNA homologies for the SLG-910 and SRK-6 genes (alleles) are shown in brackets.

The SRK-910 DNA sequence has an open reading frame of 2574 bp for a predicted protein sequence of 858 amino acids, followed by a small 3' untranslated region represented by nucleotides 2585 to 2749 (FIG. 4). Nucleotides 1 to 1315 of FIG. 4 represent the portion of the SRK-910 gene which cross-hybridized to the SLG-A14 probe used in the initial study. There are features in this sequence that are representative of SLG alleles such as the 12 cysteine residues conserved in all SLG sequences (FIG. 4, dashed line above). In addition, there are seven potential N-glycosylation sites (FIG. 4, bold-italics) in keeping with the fact that the SLG proteins are glycosylated (Takayama et al., 1986, 1989). A hydropathy plot (FIG. 5) of the predicted amino acid sequence shows a signal peptide at the N-terminal end and a transmembrane domain separating the SLG homologous N-terminus with the rest of the coding region (FIG. 4, underlined; FIG. 5). Homology comparisons (FIG. 5) of the SRK-910 SLG domain to other SLG alleles indicated that the SRK-910 allele is most closely related to its SLG counterpart at the same locus, the SLG-910 allele. At the DNA level, there is 89.9% homology between the two genes and 84.1% similarity at the amino acid level (FIG. 5). Amino acid homologies to other phenotypically strong SLG alleles range from 72% to 79% (not shown).

The predicted amino acid sequence of the 3' end of the gene, after the transmembrane domain, contains conserved amino acids found in serine/threonine protein kinases (Hanks et al., 1988). In plants, there have been three other reports of receptor kinases and all have contained the serine/threonine protein kinase consensus sequences (Walker & Zheng, 1990; Stein et al., 1991; Tobias et al., 1992). Alignment of the SRK-910 sequence to these other receptor kinases show that is most similar to the SRK-gene isolated from *B. oleracea* (FIG. 5). Since comparisons of SLG alleles from *B. oleracea* and *B. camoestris* have shown that these alleles are equally similar across species as they are within species (Dwyer et al., 1991; 07/847,564), the high level of similarity between SRK-910 (*B. camoestris* origin) and SRK-6 (*B. oleracea* origin) is not surprising. However, a comparison between these two genes of the SLG domain and kinase domain separately shows an interesting feature. In the kinase domain, the homology between the SRK-910 and SRK-6 DNA sequences is 89.6% and the amino acid similarity is 84.1% with a difference of 5.5%. In the receptor domain, the DNA homology is 84.8%; however, the amino acid similarity decreases by 9.4% to 75.4%. Since it is likely that the extracellular receptor domain determines the specificity of each allele, there appears to have been a greater selection for base substitutions in this region which alter the amino acid sequence. There is a significant, but lower level of homology to the *B. oleracea* pollen recessive SRK-2 gene and the Arabidopsis ARK-1 gene. The ARK-1 gene is not a S-locus gene because Arapidopsis, despite being closely related to the Brassica family, does not possess a self-incompatibility system. The corn ZMPK-1 gene is most distantly related to the SRK-910 gene with higher levels of homology detected in the kinase domain (FIG. 5).

Hanks et al. (1988) have shown in an alignment of other eucaryotic protein kinases that within 11 domains, there are several absolutely conserved amino acids and several conserved amino acid groups. An alignment of the eleven domains within the kinase region of the five plant receptor kinases is shown in FIG. 6 with the consensus amino acids indicated on the top line. All of the absolutely conserved amino acids (in bold) are present. In addition, the conserved amino acid groups (regular type) are also present. The two underlined regions represent consensus sequences differentiating between serine/threonine kinases and tyrosine kinases. While the sequence of the corn ZMPK-1 protein most closely represents the two consensus regions, the SRK-910 is most divergent, especially in the first consensus region (FIG. 6). The second consensus region in the SRK-910 is closer to the serine/threonine kinase consensus sequence than that found for tyrosine kinases (P-I/V-K/R-W-T/M-A-P-E). Recently, a number of protein kinases have been isolated which contain the consensus serine/threonine sequences, but demonstrate serine/threonine and tyrosine (STY) activity when tested. Seger et al. (1991) noted some sequence homologies specific to these STY kinases in domain XI. A search for these consensus sequences in domain XI of the plant kinases did not reveal any similarities.

Kinase Activity of The SRK-910 Protein

To confirm that the SRK-910 is an active kinase and to determine the specificity of the kinase activity, fusion proteins were synthesized in *E. coli* and assayed for kinase activity. The kinase domain (nucleotides 1383–2749) was placed in pGEX-3X (Smith & Johnson, 1988) which creates a protein fusion between glutathione S-transferase (GST) and the SRK-910 kinase, and in pAGEX-2T (Smith & Wildeman, in preparation) which contains two IgG binding domains from *S. aureus* protein A in front of the GST protein. These two constructs produce fusion proteins of 72 kD and 83 kD in size, respectively. Purified fusion proteins were assayed for kinase activity based on autophosphorylation in the presence of $\gamma^{32}$P-ATP. To demonstrate that phosphorylation of the fusion proteins was not the result of bacterial kinase activity, a mutant SRK-910 protein ("kinase") was also constructed by substituting an alanine residue for the invariant lysine in domain II (FIG. 6). The mutant SRK-910 protein lacked kinase activity.

A coomassie blue stain of the protein gel showed that both wild type and mutant fusion proteins of the expected sizes could be detected (FIG. 7A, Lanes 4–7, marked by dots), and were not present in the control lanes of HB101 (FIG. 7A, Lane 1), pGEX-3X (FIG. 7A, Lane 2), and pAGEX-2T (FIG. 7A, Lane 3). The smaller proteins in Lanes 4–7 are either *E. coli* proteins carried through the purification, or degradation products from the fusion proteins. An autoradiogram of the protein gel showed that only the wild-type fusion proteins were labeled with $^{32}$P (FIG. 7B, Lanes 4 and 6, marked by dots). Thus, the SRK-910 gene does contain an active kinase, and mutation of the invariant lysine to alanine resulted in loss of activity. To determine the amino acid specificity of the SRK-910 kinase, the phosphorylated fusion proteins were extracted from the protein gel and subjected to phosphoamino acid analysis. For the AGST-kinase fusion protein (83 kD), only serine and threonine residues were phosphorylated (FIG. 7C). Similar results were also seen for the GEX-kinase protein (72 kD, not shown). Phosphorylation of tyrosine residues could not be detected even after a long exposure of the autoradiogram (not shown). Thus, the SRK-910 protein encodes a serine/threonine kinase.

Expression Of The SRK-910 Gene

Figure 8A:
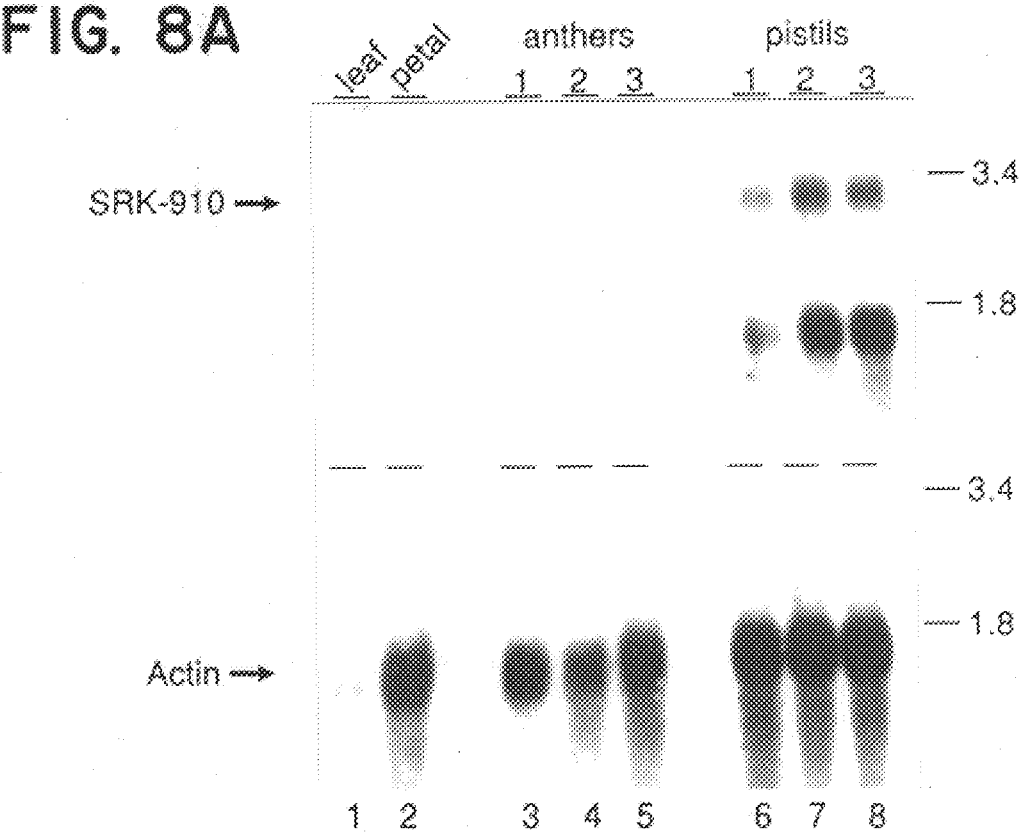
FIG. 8A is an RNA blot analysis of the SRK-910 transcripts in poly A+RNA extracted from different tissues. The anther and pistil samples were extracted from different bud sizes with Lane 1=2 to 3 mm; Lane 2=4 to 5 mm; and Lane 3=6 to 7 mm in length. After hybridization with the SRK-910 probe, the RNA blot was reprobed with an Arabidopsis actin clone to show that RNA was present in all lanes. The presence of some 18S (1.8 kb) and 25S (3.4 kb) ribosomal RNA in the poly A+ RNA preps allowed for their positions to be marked (on the right).

Poly A+RNA samples extracted from various tissues were subjected to RNA blot analysis to determine the expression patterns of the SRK-910 gene. The results showed that SRK-910 mRNA transcripts were present predominantly in the pistil at all three stages sampled. (FIG. 8A, Lanes 6–8, marked by arrow). This is a similar pattern of expression to SLG-910 gene (U.S. Ser. No. 07/847,564). However, the SRK-910 transcripts are present at considerably lower levels in comparisons to the SLG-910 transcripts (not shown). As a result of the sequence similarity between the SRK-910 and SLG-910 genes, and the high abundance of the SLG-910 message, some cross hybridization was detected in the RNA blot analysis as seen by the presence of the lower band (FIG. 8A, Lanes 6–8). Stein et al. (1991) also found that the *B. oleracea* SRK-6 gene was expressed at low levels in the anther tissue.

Figure 8B:
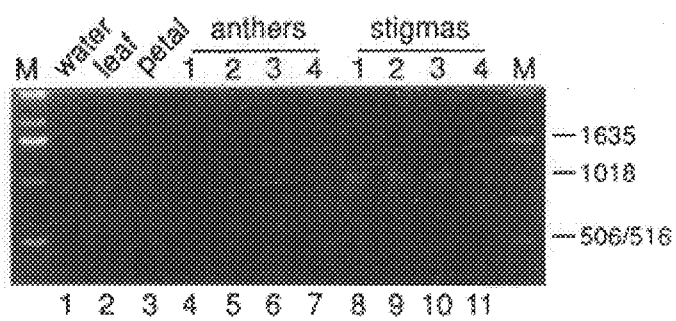
FIGS. 8B and 8C represent a PCR analysis of SRK-910 transcripts. First strand CDNA synthesized from total RNA samples were amplified for 25 cycles with the SRK-910 specific primers, primer 3 (SEQ ID No. 3) and primer 4 (SEQ ID No. 4) each having 20 bases. Ethidium bromide stain of the gel is shown in FIG. 8B. A DNA blot of the gel hybridized to the SRK-910 probe is shown in FIG. 8C. The anther and stigma (plus style) samples (Lanes 1 to 4) were extracted from different bud sizes ranging from approximately 4 to 7 mm in length. A 1 kb ladder (BRL) was used as the molecular weight markers.
Figure 8C:
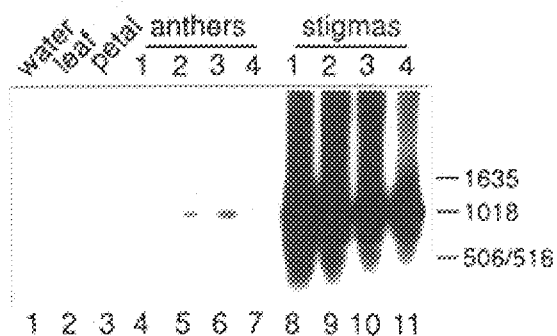

We investigated the expression of the SRK-910 gene in the same tissues using a more sensitive PCR assay. First strand cDNA synthesized from total RNA was amplified with two SRK-910 specific primers, primer 1 (nucleotides 1256–1273; SEQ ID No. 5) and primer 4 (the (−) strand for nucleotides 2304–2323; SEQ ID No. 8) that span the kinase region which contains several introns. After 25 cycles, SRK-910 PCR products were only detected in the stigma samples with ethidium bromide staining (FIG. 8B). However, DNA blot analysis of the PCR samples also revealed PCR products hybridizing to the SRK-910 probe in the anther samples, but at a much lower level than seen for the stigma samples (FIG. 8C). Hybridizing PCR products were not present in the petal and leaf samples. Thus, there is also weak expression of the SRK-910 gene in the anther.

The amino acid sequences of the receptor domain of the SRK and of the SLG presumably are crucial for differentiating between allele-specific ligand molecules synthesized in the tapetum of the male parent and present in the exine of the pollen. The predicted amino acid sequence of the SLG-910 gene shows high levels of homology to the receptor portion of the SRK-910 protein. At the amino acid level, the SRK-910 and SLG-910 proteins share 84% homology. If these two proteins are able to bind the same ligand specific to the W1 S-locus, some shared sequences unique to only these two proteins would be expected. Alignment of several SLG alleles has shown domains of conserved and variable regions (Dwyer et al., 1991). Since the variable regions are likely to be responsible for the specificity of each allele, these regions were examined for conserved amino acids between the SLG-910 and SRK-910 sequences, but obvious conserved stretches were not observed. However, single amino acids which would be brought together when the protein is folded correctly would not be easily detected.

The carboxy-half of the SRK-910 protein was found to phosphorylate only serine and threonine residues and did not appear to phosphorylate tyrosine residues as demonstrated for STY protein kinases. When the kinase domains from the plant receptor kinases were aligned, in addition to the serine/threonine consensus sequences, they contained all of the conserved amino acids that have been found in protein kinases isolated from other eucaryotes. Some of these conserved amino acids have been implicated in ATP binding or proton transfer, and thus are important for the enzyme activity (Hanks et al., 1988). In the case of the invariant lysine in domain II, we have demonstrated that altering this amino acid will also abolish kinase activity in the SRK-910 protein.

SLG proteins have been found outside of the cell membrane and localized to the cell wall of the stigma papillae cells (Kandasamy et al., 1989). In the present invention, the structure of the SRK predicted protein sequence indicates that it is localized in the cell membrane. This type of truncated secreted receptor and transmembrane receptor combination has been detected in other systems. However, in these other examples, the truncated receptor has been generated by alternate splicing of the same gene producing the transmembrane receptor and consequently, the two protein products are identical or nearly identical in sequence (Johnson et al., 1990; Petch et al., 1990). The precise role of these truncated receptors in signal transduction is not known. In one example, there is a differential expression of the truncated and full length receptors leading to the proposition that the truncated receptors may represent another level of regulation to modulate ligand responsiveness by the transmembrane receptor (Petch et al., 1990). In the case of the growth hormone receptor, the truncated receptor represents the growth hormone serum binding protein (Leung et al., 1987). Since plants also have a thick cell wall surrounding the cell membrane, the S-locus glycoproteins (SLG) may serve to recruit ligand molecules for the S-locus serine/threonine receptor kinases.

Unless signal transduction occurs through interactions between the allele specific SLG and SRK proteins, a third protein, the ligand which activates the receptor kinase must be required. The highly localized self-incompatibility response suggests that its expression would be anther specific and would have evolved co-linearly with the SLG and SRK genes at the S-locus.

While the immediate downstream targets of the activated receptor serine/threonine kinase are not known, one of the rapid responses that has been clearly documented is the deposition of (1,3)-β-glucan (callose) in the stigma papillae cell in contact with the self-incompatible pollen (Heslop-Harrison et al., 1974).

Introduction Of The Isolated cDNAs For The SRK-910 And SLG-910 Alleles Into Plants, Plants Cells And/Or Plant Protoplasts Both the SRK-910 allele and the SLG-910 allele (U.S. Ser. No. 07/847,564) have been shown to segregate with the SI-phenotype in Brassica. Additionally, neither gene appears to be present in self-compatible plants. Both genes show a tissue specific expression pattern in SI plants which corresponds to the tissues responsible for self-incompatibility in Brassica. The specific association between these genes and their expression with the SI phenotype in plants, clearly establishes the importance of these genes in the self-incompatibility mechanism of Brassica.

On this basis, the present invention also relates to a transfer vector comprising the isolated cDNA of the SRK-allele (SEQ ID No. 1) which is useful in the transformation of SC plants, plant cells from SC plants and/or protoplasts from SC plants which are capable of expressing the SI phenotype. Preferably, the transfer vector includes the isolated cDNA from two alleles that are associated with self-incompatibility, i.e., the cDNA for the SLG-910 allele, which is disclosed in our parent application U.S. Ser. No. 07/847,564, and the cDNA for the SRK-910 allele (SEQ ID No. 1), which is taught herein.

The vector of the present invention may be introduced into SC plants, plant cells and/or plant protoplasts by standard methodologies including but not limited to calcium-phosphate co-precipitation techniques, protoplast fusion, electroporation, microprojectile mediated transfer, by infection with bacteria (e.g., *Agrobacterium tumifaciens*), viruses or other infectious agents capable of delivering nucleic acids to recipient plants, plant cells and/or plant protoplasts capable of expressing the SI genes and the SI phenotype.

By way of example, the bacteria *Agrobacterium tumifaciens* may be used to introduce the vectors of the present invention into SC plants, plant cells and/or plant protoplasts. More specifically, the isolated SRK-910 (SEQ ID No. 1) and SLG-910 (U.S. Ser. No. 07/847,564) cDNAs may be cloned into the Ti plasmid pBI101.2 by standard cloning procedures. The chimeric plasmid comprising pBI101.2 and the cDNAs for SRK-910 and SLG-910 may be introduced into *Agrobacterium tumifaciens* LBA4404 (Oomstal, Gene 14; 33–50, 1981) by standard transformation techniques well known in the art. (Horsh et al., Science 277:1229–1231, 1985; Arnoldo, M., et al., Genome [in press]). The resulting *Agrobacterium tumifaciens* may then be used to introduce the SI cDNA into SC plants, plant tissues or plant protoplasts of Brassica by standard infection procedures.

It is contemplated that the introduction of a transfer vector carrying the cDNAs for both the SRK-910 and the SLG-910 alleles, such as those described above, into SC plants, plant cells and/or plant protoplasts will result in the expression of the SI phenotype in plants which were previously self-compatible.

Method For The Rapid Screening of Brassica Seedlings For the Presence Of The SRK-910 Allele In order to screen Brassica seedlings for the presence of a particular SI allele, the plants being tested are typically grown to flowering and then crossed to tester plant lines carrying known alleles as described above. This process is both time-consuming and expensive. In order to overcome these problems, the present invention also relates to a method for the rapid screening of Brassica seedlings for the presence of SRK-910 allele. The method employs the polymerase chain reaction to amplify the genomic DNA obtained from the Brassica seedling of interest. To have specificity for the SRK-910 allele, the method utilizes oligonucleotide probes selected from unique regions of the SRK-910 allele. Suitable nucleotide probes for detecting the presence of the allele are primers 1, 2, 3, or 4 as taught herein. In particular, the method for screening a Brassica seedling for the SRK-910 allele comprises the steps of:

a) obtaining genomic DNA from the tissue of a Brassica seedling suspected of having the SRK-910 allele;

b) combining the genomic DNA with a (+) strand oligonucleotide and a (−) strand oligonucleotide that are both SRK-910 specific and capable of priming the amplification of the SRK-910 allele, the oligonucleotides comprising:
  i. a (+) strand oligonucleotide having the sequence TCCGGAATTACTTTGATGAC (SEQ ID No. 7), and a (−) strand oligonucleotide having the sequence GAAAGGTTGCTGGTAATGAT (SEQ ID No. 8); or
  ii. a (+) strand oligonucleotide having the sequence AGTAACGATGAGTATTTGGC (SEQ ID No. 5), and a (−) strand oligonucleotide having either the sequence CATATTGAAGGGCTTGAAAC (SEQ ID No. 6) on the sequence GAAAGGTTGCTGGTAATGAT (SEQ ID No. 8);
c) amplifying the allele using the polymerase chain reaction to render the allele detectable; and
d) determining the presence of the SRK-910 allele by detecting the PCR amplification products that are specific for the SRK-910 allele.

In this method, genomic DNA is prepared from seedlings by the method of Edwards and Thompson, (Nucl. Acids. Res. 19:1349, 1991.) Genomic DNA is then amplified in a polymerase chain reaction using a pair of specific primers that are preferably oriented in opposite directions. The step of determining the presence of the allele, via its amplification products, may be accomplished by any of the standard detection techniques already described herein. It is also within the scope of the present invention to label the SRK-910 probe or a specific oligonucleotide, such as those recited in Step (b), for use in detecting the PCR amplification products. The use of radioactive labels, such as $^{32}$p, for the labeling of nucleotide probes is well known in the art.

Because the SRK-910 gene and self-incompatibility segregate together, the present invention is further directed to screening a Brassica seedling for self-incompatibility comprising the steps of:
  a) obtaining genomic DNA from the tissue of a Brassica seedling suspected of having the self-incompatibility phenotype;
  b) combining the genomic DNA with a (+) strand oligonucleotide and a (−) strand oligonucleotide that are both SRK-910 specific and capable of priming the amplification of the SRK-910 allele, the oligonucleotides comprising:
    i. a (+) strand oligonucleotide having the sequence TCCGGAATTACTTTGATGAC (SEQ ID No. 7), and a (−) strand oligonucleotide having the sequence GAAAGGTTGCTGGTAATGAT (SEQ ID No. 8); or
    ii. a (+) strand oligonucleotide having the sequence AGTAACGATGAGTATTTGGC (SEQ ID No. 5), and a (−) strand oligonucleotide having either the sequence CATATTGAAGGGCTTGAAAC (SEQ ID No. 6) on the sequence GAAAGGTTGCTGGTAATGAT (SEQ ID No. 8);
  c) amplifying the SRK-910 allele, which is associated with the self-incompatibility phenotype, using the polymerase chain reaction (PCR) technique to render the allele detectable; and
  d) determining the presence of the self-incompatibility phenotype by detecting the presence of the PCR amplification products that are specific for the SRK-910 allele.

EXPERIMENTAL PROCEDURES

1. Cloning Of The SRK-910 Gene

PCR amplification of the 800bp internal genomic fragment has been described above and in our co-pending parent application, U.S. Ser. No. 07/847,564, which is incorporated herein by reference. For the 3' RACE procedure, we utilized the cDNA synthesis, the $dT_{17}$-Adaptor (SEQ ID No. 9) and Adaptor (SEQ ID No. 10) primers of FIG. 10, and the PCR amplification as described in our parent application (U.S. Ser. No. 07/847,564), except that approximately 400 ng of poly A+ RNA was used for the cDNA synthesis. After the first round of amplification with the SRK-910 specific primer, primer 1 (SEQ ID No. 5), a specific band was not detected. The resulting products (faint smears) were fractionated on a 1% low melting-point agarose gel and agarose plugs were removed with pasteur pippettes (Zintz & Beebe, 1991) in the range of 1.5 to 5 kb. The DNA-containing agarose plugs were melted at 70° C. for 10 minutes and subjected to a second round of PCR amplification using 200 nM each of the Adaptor (SEQ ID No. 10) and SRK-910 specific primer, primer 3 (SEQ ID No. 7) for 30 cycles.

For the inverse PCR, 100 ng of size fractionated (3.6 to 3.9 kb), Hind III digested, W1 genomic DNA was ligated under dilute conditions promoting circularization (Ochman et al., 1988). After 40 cycles, the PCR reaction was precipitated with ethanol and size fractionated on a low melting point agarose gel. A faint band could be detected at approximately 3.5 kb in size, and agarose plugs were removed as described above and amplified for 21 cycles. All PCR products were cloned into pBluescript (Stratagene, LaJolla, Calif.) and sequenced as described herein. Two to three different clones from separate PCR reactions were sequenced for each section to solve any discrepancies in the SRK-910 sequence resulting from Taq polymerase errors. DNA and protein sequence analysis was carried out using the DNASIS and PROSIS software (Pharmacia, Piscataway, N.J.).

2. Intron Analysis

First strand cDNA primed with primer 4 (i.e., nucleotides complimentary to 2304-2323; SEQ ID No. 8), the 3' RACE cDNA clones, and a W1 genomic DNA sample were amplified with two primers (20 bp each) encompassing nucleotides 1378 to 2323 of the SRK-910 gene. The resulting PCR products were gel-purified from low molecular weight PCR products and digested with Alu I. The digested samples were labelled with $^{35}$S-dATP by an exchange reaction with the Klenow polymerase fragment (Sambrook et al., 1989), and size fractionated on a 5% polyacrylamide gel. The gel was then dried and exposed to X-ray film.

3. Fusion Proteins and Kinase Assays

Mutation of the invariant lysine to alanine was carried using PCR mutagenesis. Two overlapping regions (nucleotides 1256–1681; and nucleotides 1378–1779) were amplified with one of the inside primers (nucleotides 1660–1681) introducing the AAAGCA change. The two separate PCR fragments (approximately 400 bp in length) were mixed together and reamplified with the outside primers (nucleotides 1256–1779) to produce a 523 bp fragment which was then cloned and sequenced. With this strategy, half of the clones carried the introduced mutation. A 400 bp Bcl I/Eco RI fragment (nucleotides 1383–1761) containing the mutation was then cloned into the kinase domain to replace the wild type sequence. The GST fusions were made using the 3' end of the clone starting at the Bcl I site which occurs near the end of the transmembrane domain. The 5' end (Bcl I) was placed in frame to the Sma I site in a pAGET-2T (Smith & Wildeman, in preparation).

For the kinase assays, 50 ml HB101 cultures carrying the various fusion constructs were grown at 37° C. to an $OD_{600}$ of 0.6 (faster growing cultures were diluted during growth). IPTG was then added to a final concentration of 1 mM and the cultures were incubated at 37° C. for one hour. Purification of the fusion proteins on glutathione agarose beads was carried out essentially as described in Smith & Johnson (1988), except that instead of PBS, the extraction buffer of Douville et al (1992) was used for resuspension and washes. In addition, the protein extracts were mixed with the glutathione agarose beads for 30 minutes at room temperature. Following the washes, the agarose beads containing the fusion proteins were washed an additional two times with the kinase buffer (30 mM Tris pH 7.5, 20 mM HEPES pH 7.1, 10 mM $MgCl_2$, 2 mM $MnCl_2$; Douville et al. 1992) and resuspended in a final volume of 50 ul kinase buffer. 25 $\mu Ci$ of $\gamma^{32}$-P-ATP (6000 Ci/mmol) was added to each sample and left at room temperature for 30 minutes. The beads were spun down, resuspended in 20 $\mu l$ of 2×sample buffer, boiled for 5 minutes and electrophoresed through an 8.5% SDS-PAGE gel. Subsequently, the SDS-PAGE gel was stained with coomassie blue, dried down and exposed overnight to X-ray film at −70° C. The fusion proteins which could be detected by the coomassie blue stain were excised and extracted from the gel, and subjected to phosphoamino acid analysis as described in Cooper et al. (1983) and Boyle et al. (1991).

4. RNA and DNA Blot Analysis, And PCR Expression Analysis

The poly A+RNA samples for the RNA blot analysis were extracted using the Micro-FastTract mRNA isolation kits (Invitrogen). The procedures for gel electrophoresis and blot hybridization were as previously described (U.S. Ser. No. 07/847,564). Following hybridization, the blots were washed twice in 0.1× SSC and 0.1% SDS for 30 minutes. The washing temperatures were 67° C. for the SRK-910 probe and 50° C. for the Arabidopsis actin probe.

To examine the expression of SRK-910 gene using PCR, total RNA samples were extracted using the method of Jones et al., (1985). Ten micrograms of total RNA was used for first strand cDNA synthesis using random hexamers and the procedure of Harvey and Darlison (1991). Three PCR reactions were set up from each batch of cDNA, and allowed to amplify for 25, 35, and 45 cycles, respectively. One-quarter of the PCR reaction was subjected to gel-electrophoresis. The PCR products were visualized with ethidium bromide staining and then subjected to DNA blot analysis.

REFERENCES

1. Aaronson, S. A. (1991). Growth factors and cancer. Science 254, 1146–1153.
2. Bateman, A. J. (1955). Self-Incompatibility systems in angiosperms. III. Cruciferae. Heredity 9, 53–68.
3. Boyes, D. C., Chen, C. H. Tantikanjana, T., Esch, J. J. and Nasrallah, J. b. (1991). Isolation of a second S-locus-related cDNA from Brassica oleracea: Genetic relationships between the S-locus and two related loci. Genetics 127, 221–228.
4. Boyle, W. J., Van der Geer, P., and Hunter, T. (1991). Phosphopeptide maping and phosphoamino acid analysis by two-dimensional separation on thin-layer cellulose plates. Meth. Enzymol. 201, 110–149.
5. Cadena, D. L., and Gill, G. N. (1992). Receptor tyrosine kinases. FASEB J. 6, 2332–2337.
6. Cantley, L. C., Auger, K. R., Carpenter, C., Duckworth, B., Grazianli, A., Kapeller, R. and Soltoff, S. (1991). Oncogenes and signal transduction. Cell 64, 281–302.
7. Cooper, J. A. Sefton, B. M. and Hunter, T. (1983). Detection and quantification of phosphotyrosine in proteins. Meth. Enzymol. 99, 387–402.
8. Douville, E. M., Afar, D. E. H., Howell, B. W., Letwin, K., Tannock, L., Ben-David, Y., Pawson, T. and Bell, J. C. (1992). Multiple DNAs encoding the esk kinase predict transmembrane and intracellular enzyme isoforms. Mol. Cell. Biol. 12, 2861–2689.
9. Downey, R. K. and Rakow, G. F. W. (1987). Rapeseed and mustard. Pages 437–486 in Fehr, W. R. (ed.) Principles of Cultivar Development, Macmillan Publishing Co., New York.
10. Dwyer, K. G., Balent, M. A., Nasrallah, J. B., Nasrallah, M. E. (1991). DNA sequences of self-incompatibility genes from Brassica compestris and B. oleracea: polymorphism predating speciation. Plant Mol. Biol. 16, 481–486.
11. Frohman, M. A., Dush, M. K., Martin, G. R. (1988). Rapid production of full-length cDNAs from rare transcripts: Amplification using a single gene-specific oligonucleotide primer. Proc. Natl. Acad. Sci. 85, 8998–9002.
12. Gaude, T. and Dumas, C. (1987). Molecular and cellular events of self-incompatibility. Int. Rev. Cytol. 107, 333–336.
13. Goring, D. R., Banks, P., Beversdorf, W. D. and Rothstein, S. J. (1992a). Use of the polymerase chain reaction to isolate an S-locus glycoprotein cDNA introgressed from B. camoestris into B. napus ssp. oleifera. Mol. Gen. Genet., in press.
14. Goring, D. R., Banks, P., Fallis, L., Baszczynski, C. L., Beversdorf, W. D. and Rothstein, S. J. (1992b). Identification of an S-locus glycoprotein allele introgressed from B. napus ssp. rapifera to B. napus ssp. oleifera. Plant J., accepted.
15. Gowers, S. (1981). Self-pollination in swedes (Brassica napus ssp. rapifera) and its implications for cultivar production. Euphytica 30, 813, 817.
16. Hanks, S., Quinn, A. M., and Hunter, T. (1988). The protein kinase family: Conserved features and deduced phylogeny of the catalytic domains. Science 241, 42–52.
17. Harvey, R. J., Darlison, M. G. (1991). Random-primed cDNA synthesis facilitates the isolation of multiple 5'-cDNA ends by RACE. Nucl. Acid Res. 19, 4002.
18. Heslop-Harrison, J., Knox, R. B., Heslop-Harrison, Y. (1974). Pollen-wall proteins: exine-held fractions associated with the incompatibility response in Cruciferae. Theor. Appl. Genet. 44, 133–137.
19. Hinata, K., Nishio, T. (1978). S allele specificity of stigma protein in Brassica oleracea and Brassica campestris. Heredity 41, 93–100.
20. Johnson, D. E., Lee, P. L., Lu, J. and Williams, L. T. (1990). Diverse forms of a receptor for acidic and basic fibroblast growth factors. Mol. Cell. Biol. 10, 4728–4736.
21. Jones, J. D. G., Dunsmuir, P. and Bedbrook, J. (1985). High level expression of introduced chimeric genes in regenerated transformed plants. EMBO J. 4, 2411–2418.
22. Kandasamy, M. K., Paolillo, D. J., Faraday, C. D., Nasrallah, J. B., and Nasrallah, M. E. (1989). The S-locus specific glycoproteins of Brassica accumulate 22. ...in the cell wall of developing stigma papillae. Dev. Biol. 134, 462–472.
23. Karin, M. (1992). Signal transduction from cell surface to nuclease in development and disease. FASEB J. 6, 2581–2590.
24. Kauss, H. (1985). Callose biosynthesis as a $Ca^{2+}$-regulated process and possible relations to the induction of other metabolic changes. J. Cell Sci. Suppl. 2, 89–103.
25. Lalonde, B. A., Nasrallah, M. E., Dwyer, K. g. Chen, C. H., Barlow, B. and Nasrallah, J. b. (1989). A highly conserved Brassica gene with homology to the S-locus-specific glycoprotein structural gene. Plant Cell 1, 249–258.
26. Leung, D. W., Spencer, S. A., Cachianes, G., Hammonds, R. G., Collins, C., Henzel, W. J., Barnard, R., Waters, M. J. and Wood, W. I. (1987). Growth hormone receptor and serum binding protein: purification, cloning and expression. Nature 330, 537–543.
27. Lin, H. Y., Wang, X. F., Ng-Eaton, E., Weinberg, R. A., and Lodish, H. F. (1992). Expression cloning of a TGF-type II receptor, a functional transmembrane serine/threonine kinase. Cell 68, 775–785.
28. Maga, E. A. and Richardson, T. (1991). Amplification of a 9.0-kb fragment using PCR, Biotechniques 11, 185–186.
29. Mackay, G. R. (1977). The introgression of S alleles into forage rape Brassica napus L. from turnip Brassica campestris ssp. rapifera. Euphytica 26, 511–519.
30. Nasrallah, M. E., Barber, J. T., Wallace, D. H. (1970). Self incompatibility proteins in plants: detection, genetics and possible mode of action. Heredity 25, 23–27.
31. Nasrallah, J. b., Kao, T. H., Chen, C. H., Goldberg, M. L., Nasrallah, M. E. (1987). Amino-acid sequence of glycoproteins encoded by three alleles of the S-locus of Brassica oleracea. Nature 326, 617–619.
32. de Nettancourt, D. (1977). Incompatibility in Angiosperms. Springer-Verlag, New York.
33. Nishio, T., Toriyama, K., Sato, T., Kandasamy, M. K., Paolillo, D. J., Nasrallah, J. B., and Nasrallah, M. E. (1992). Expression of S-locus glycoprotein genes from Brassica oleracea and B. camoestris in transgenic plants of self-compatible B. napus cv Westar. Sex. Plant Reprod. 5, 101–109.
34. Ochman, H., Gerber, A. S., and Hartl, D. L. (1988). Genetic applications of an inverse polymerase chain reaction. Genetics 120, 621–623.
35. Ockendon, D. J. (1974). Distribution of self-incompatibility alleles and breeding structure of open-pollinated cultivars of Brussel sprouts. Heredity 33, 159–171.
36. Ockendon, D. J. (1982). An S-allele survey of cabbage (Brassica oleracea var. capitata). Euphytica 31, 325–331.
37. Olsson, G. (1960). Self-incompatibility and outcrossing in rape and white mustard. Hereditas 46, 241–252.
38. Petch, L. A., Harris, J., Raymond, V. W., Blasband, A., Lee, D. C. and Earp, H. S. (1990). A truncated, secreted form of the epidermal growth factor receptor is encoded by an alternatively spliced transcript in normal rat tissue Mol. Cell. Biol. 10, 2973–2982.
39. Sato, T., Thorsness, N. K., Kandasamy, M. K., Nishio, T., Hirai, M., Nasrallah, J. B. and Nasrallah, M. E. (1991). Activity of an S locus gene promoter in pistils and anthers of transgenic Brassica. Plant Cell 3, 867–876.
40. Scutt, C. and Croy, R. R. D. (1992). An S5 self-incompatibility allele-specific CDNA sequence from Brassica oleracea shows high homology to the SLR2 gene. Mol. Gen. Genet. 232, 240–246.
41. Seger, R., Ahn, N. G., Boulton, T. G., Yancopoulos, G. D., Panayotatos, N., Radziejewska, E., Ericcson, L., Bratlien, R. L., Cobb, M. H., and Krebs, E. G. (1991). Microtubule-associated protein 2 kinases, ERK1 and ERK2, undergo autophosphorylation on both tyrosine and threonine residues: Implications for their mechanism of activation. Proc. Natl. Acad. Sci. U.S.A. 88, 6142–6149.
42. Smith, D. and Johnson, K. S. (1988). Single-step purification of polypeptides expressed in Escherichia coli as fusions with glutathione S-transferase. Gene 67, 31–40.
43. Sambrook, J., Fritsch, E. F. and Maniatis, T. (1989). Molecular cloning: A laboratory manual. 2nd ed. Cold Spring Harbor Laboratory. Press.
44. Stein, J. C., Howlett, B., Boyes, D. C., Nasrallah, M. E., Nasrallah, J. B. (1991). Molecular cloning of a putative receptor protein kinase gene encoded at the self-incompatibility locus of Brassica oleracea. Proc. Natl. Acad. Sci. 88, 8816–8820.
45. Takayama, S., Isogai, A., Tsukamoto, C., Ueda, Y., Hinata, K., Okazaki, K., Koseki, K., Suzuki, A. (1986). Structure of carbohydrate chains of S-glycoproteins in Brassica campestris associated with self-incompatibility. Agric. Biol. Chem. 50, 1673–1676.
46. Takayama, S., Isogal, A., Tsukamoto, C., Shiozawa, H., Ueda, Y., Hanata, K., Okazaki, K., Koseki, K., Suzuki, A. (1989). Structures of N-glycosidic saccharide chains in S-glycoproteins, products of S-genes associated with self-incompatibility in Brassica capestris. Agric. Biol. Chem. 53, 713–722.
47. Thompson, K. F., Talor, J. P. (1966). Non-linear dominance relationships between S-alleles. Heredity 21, 345–362.
48. Tobias, C. M., Howlett, B. and Nasrallah, J. B. (1992). An Arabidopsis thaliana gene with sequence similarity to the S-locus receptor kinase of Brassica oleracea. Plant Physiol. 99, 284–309).
49. Trik, M., Flavell, R. B. (1989). A homozygous S genotype of Brassica oleracea expresses two S-like genes. Mol. Gen. Genet. 218, 112–117.
50. Ullrich, A., and Schlessinger, J. (1990). Signal transduction by receptors with tyrosine kinase activity. Cell 61, 203–212.
51. Walker, J. C. and Zhang, R. (1990). Relationship of a putative receptor protein kinase from maize to the S-locus glycoproteins of Brassica. Nature 345, 743–746.
52. Zintz, C. B., Beebe, D. C. (1991). rapid re-amplification of PCR products purified in low melting point agarose gels. BioTechniques 11, 158–162.
53. Zuberi, M. I., and Dickinson, H. G. (1985). Pollen-stigma interaction in Brassica III. Hydration of the pollen grains. J. Cell Sci. 76, 321–336.

What is claimed is:

1. An isolated DNA molecule comprising the nucleotide sequence of SEQ ID No. 1.

2. The DNA molecule of claim 1 consisting of the nucleotide sequence of SEQ ID No. 1.

3. The DNA molecule of claim 2, wherein said DNA molecule encodes a serine/threonine kinase.

4. An isolated DNA molecule encoding either a protein having the amino acid sequence of SEQ ID No. 2 or a kinase active fragment of said protein.

5. A DNA probe comprising an oligonucleotide having a nucleotide sequence selected from the group consisting of:
AGTAACGATGAGTATTTGGC (SEQ ID No. 5);
CATATTGAAGGGCTTGAAAC (SEQ ID No. 6);
TCCGGAATTACTTTGATGAC (SEQ ID No. 7); and
GAAAGGTTGCTGGTAATGAT (SEQ ID No. 8).

6. An isolated protein having either the amino acid sequence of SEQ ID No. 2 or a portion of said sequence that encodes a kinase active polypeptide.

7. A method for screening a Brassica seedling suspected of having the SRK-910 allele comprising the steps of:
  a) obtaining genomic DNA from the tissue of a Brassica seedling suspected of having the SRK-910 allele;
  b) combining the genomic DNA with a (+) strand oligonucleotide and a (−) strand oligonucleotide that are both SRK-910 specific and capable of acting as primers for the amplification of the SRK-910 allele, said pair of oligonucleotides comprising, either,
    i. a (+) strand oligonucleotide having the sequence TCCGGAATTACTTTGATGAC (SEQ ID No. 7), and a (−) strand oligonucleotide having the sequence GAAAGGTTGCTGGTAATGAT (SEQ ID No. 8); or
    ii. a (+) strand oligonucleotide having the sequence AGTAACGATGAGTATTTGGC (SEQ ID No. 5), and a (−) strand oligonucleotide having either the sequence CATATTGAAGGGCTTGAAAC (SEQ ID No. 6) or the sequence GAAAGGTTGCTGGTAAT-GAT (SEQ ID No. 8);
  c) amplifying the allele using the polymerase chain reaction to render the allele detectable; and
  d) determining the presence of the SRK-910 allele by detecting the PCR amplification products that are specific for the SRK-910 allele.

8. The method of claim 7 wherein one parent or ancestor of the Brassica seedling is in the W1 Brassica line.

9. A method for screening a Brassica seedling for the presence of the self-incompatibility phenotype, comprising the steps of:
  a) obtaining genomic DNA from the tissue of a Brassica seedling suspected of having the self-incompatibility phenotype;
  b) combining the genomic DNA with a (+) strand oligonucleotide and a (−) strand oligonucleotide that are both SRK-910 specific and capable of acting as primers for the amplification of the SRK-910 allele, said pair of oligonucleotides comprising, either,
    i. a (+) strand oligonucleotide having the sequence TCCGGAATTACTTTGATGAC (SEQ ID No. 7), and a (−) strand oligonucleotide having the sequence GAAAGGTTGCTGGTAATGAT (SEQ ID No. 8); or
    ii. a (+) strand oligonucleotide having the sequence AGTAACGATGAGTATTTGGC (SEQ ID No. 5), and a (−) strand oligonucleotide having either the sequence CATATTGAAGGGCTTGAAAC (SEQ ID No. 6) or the sequence GAAAGGTTGCTGGTAATGAT (SEQ ID No. 8);
  c) amplifying the SRK-910 allele, which is associated with self-incompatibility, using the polymerase chain reaction (PCR) technique to render the allele detectable; and
  d) determining the presence of the self-incompatibility phenotype by detecting the presence of the PCR amplification products that are specific for the SRK-910 allele.

10. The method of claim 9 wherein one parent or ancestor of the Brassica seedling is in the W1 Brassica line.

11. A vector comprising the DNA molecule of claim 1.

12. The vector of claim 11 further comprising a DNA molecule that encodes the SLG-910 gene.

13. The vector of claim 12 further comprising the Ti plasmid.

14. The transfer vector of claim 13 wherein the Ti plasmid comprises pBI101.2.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
    ( A ) LENGTH: 2749 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Brassica napus
    ( B ) STRAIN: oleifera
    ( C ) INDIVIDUAL ISOLATE: W1

( v i i i ) POSITION IN GENOME:
    ( A ) CHROMOSOME/SEGMENT: S- locus ( i x ) FEATURE:
    ( A ) NAME/KEY: CDS
    ( B ) LOCATION: 1..2574

( x ) PUBLICATION INFORMATION:
    ( A ) AUTHORS: GORING, DAPHNE
           ROTHSTEIN, STEVEN J.
    ( B ) TITLE: THE S-LOCUS RECEPTOR KINASE GENE IN A
           SELF- INCOMPATIBLE BRASSICA NAPUS LINE ENCODES A
           FUNCTIONAL SERINE/THREONINE KINASE
    ( K ) RELEVANT RESIDUES IN SEQ ID NO:1: FROM 1 TO 2749

( x i ) SEQUENCE DESCRIPTION: SEQ ID NO:1:

```
ATG  AAA  GGA  GTA  AGA  AAA  ACC  TAC  GAT  AGT  TCT  TAC  ACT  TTA  TCC  TTC       48
Met  Lys  Gly  Val  Arg  Lys  Thr  Tyr  Asp  Ser  Ser  Tyr  Thr  Leu  Ser  Phe
 1             5                        10                       15

TTG  CTC  GTC  TTT  TTC  GTC  ATG  TTT  CTA  TTT  CAT  CCT  GCC  CTT  TCG  ATC       96
Leu  Leu  Val  Phe  Phe  Val  Met  Phe  Leu  Phe  His  Pro  Ala  Leu  Ser  Ile
              20                        25                       30

CAT  ATC  AAC  ACT  TTG  TCG  TCT  ACA  GAA  TCT  CTT  ACA  ATC  TCA  AAC  AAC      144
His  Ile  Asn  Thr  Leu  Ser  Ser  Thr  Glu  Ser  Leu  Thr  Ile  Ser  Asn  Asn
          35                            40                   45

AGA  ACA  CTT  GTG  TCT  CCA  GGT  AAT  GTC  TTC  GAG  CTC  GGC  TTC  TTT  AGA      192
Arg  Thr  Leu  Val  Ser  Pro  Gly  Asn  Val  Phe  Glu  Leu  Gly  Phe  Phe  Arg
      50                        55                        60

ACC  ACC  TCA  AGT  TCT  CGT  TGG  TAT  CTC  GGG  ATA  TGG  TAC  AAG  AAT  TTG      240
Thr  Thr  Ser  Ser  Ser  Arg  Trp  Tyr  Leu  Gly  Ile  Trp  Tyr  Lys  Asn  Leu
 65                       70                        75                       80

CCC  TAT  AAA  ACC  TAT  GTT  TGG  GTT  GCA  AAC  AGA  GAT  AAC  CCT  CTC  TCC      288
Pro  Tyr  Lys  Thr  Tyr  Val  Trp  Val  Ala  Asn  Arg  Asp  Asn  Pro  Leu  Ser
                      85                        90                       95

GAT  TCC  ATT  GGT  ACG  CTC  AAA  ATC  TCC  AAC  ATG  AAC  CTT  GTC  CTC  CTC      336
Asp  Ser  Ile  Gly  Thr  Leu  Lys  Ile  Ser  Asn  Met  Asn  Leu  Val  Leu  Leu
               100                      105                     110

GAC  CAC  TCT  AAT  AAA  TCT  GTT  TGG  TCG  ACG  AAT  CTG  ACT  AGA  GGA  AAT      384
Asp  His  Ser  Asn  Lys  Ser  Val  Trp  Ser  Thr  Asn  Leu  Thr  Arg  Gly  Asn
          115                           120                     125

GAG  AGA  TCT  CCG  GTG  GTG  GCA  GAG  CTT  CTG  GAG  AAC  GGA  AAC  TTC  GTC      432
Glu  Arg  Ser  Pro  Val  Val  Ala  Glu  Leu  Leu  Glu  Asn  Gly  Asn  Phe  Val
      130                       135                       140
```

-continued

| | | | | | | | | | | | | | | | | |
|---|---|---|---|---|---|---|---|---|---|---|---|---|---|---|---|---|
| ATT | CGA | TAC | TCC | AAT | AAC | AAC | AAC | GCA | AGT | GGA | TTC | TTG | TGG | CAA | AGT | 480 |
| Ile | Arg | Tyr | Ser | Asn | Asn | Asn | Asn | Ala | Ser | Gly | Phe | Leu | Trp | Gln | Ser | |
| 145 | | | | 150 | | | | | 155 | | | | | | 160 | |
| TTC | GAT | TTC | CCT | ACA | GAT | ACT | TTG | CTT | CCA | GAG | ATG | AAA | CTA | GGC | TAC | 528 |
| Phe | Asp | Phe | Pro | Thr | Asp | Thr | Leu | Leu | Pro | Glu | Met | Lys | Leu | Gly | Tyr | |
| | | | | 165 | | | | | 170 | | | | | 175 | | |
| GAC | CGC | AAA | AAA | GGG | CTG | AAC | AGA | TTC | CTT | ACA | GCA | TGG | AGA | AAT | TCA | 576 |
| Asp | Arg | Lys | Lys | Gly | Leu | Asn | Arg | Phe | Leu | Thr | Ala | Trp | Arg | Asn | Ser | |
| | | | 180 | | | | | 185 | | | | | 190 | | | |
| GAT | GAT | CCC | TCA | AGC | GGG | GAA | ATC | TCG | TAC | CAA | CTA | GAC | ACT | CAA | AGA | 624 |
| Asp | Asp | Pro | Ser | Ser | Gly | Glu | Ile | Ser | Tyr | Gln | Leu | Asp | Thr | Gln | Arg | |
| | | 195 | | | | | 200 | | | | | 205 | | | | |
| GGA | ATG | CCT | GAG | TTT | TAT | CTA | TTG | AAA | AAC | GGC | GTA | CGA | GGC | TAC | CGG | 672 |
| Gly | Met | Pro | Glu | Phe | Tyr | Leu | Leu | Lys | Asn | Gly | Val | Arg | Gly | Tyr | Arg | |
| | 210 | | | | | 215 | | | | | 220 | | | | | |
| AGT | GGT | CCA | TGG | AAT | GGA | GTC | CGA | TTT | AAT | GGC | ATA | CCA | GAG | GAC | CAA | 720 |
| Ser | Gly | Pro | Trp | Asn | Gly | Val | Arg | Phe | Asn | Gly | Ile | Pro | Glu | Asp | Gln | |
| 225 | | | | | 230 | | | | | 235 | | | | | 240 | |
| AAG | TTG | AGT | TAC | ATG | GTG | TAC | AAC | TTC | ACA | GAT | AAT | AGT | GAG | GAG | GCT | 768 |
| Lys | Leu | Ser | Tyr | Met | Val | Tyr | Asn | Phe | Thr | Asp | Asn | Ser | Glu | Glu | Ala | |
| | | | | 245 | | | | | 250 | | | | | 255 | | |
| GCT | TAT | ACA | TTT | CGA | ATG | ACC | GAC | AAG | AGC | ATC | TAC | TCG | AGA | TTG | ATA | 816 |
| Ala | Tyr | Thr | Phe | Arg | Met | Thr | Asp | Lys | Ser | Ile | Tyr | Ser | Arg | Leu | Ile | |
| | | | 260 | | | | | 265 | | | | | 270 | | | |
| ATA | AGT | AAC | GAT | GAG | TAT | TTG | GCG | CGA | CTA | ACG | TTC | ACT | CCG | ACA | TCA | 864 |
| Ile | Ser | Asn | Asp | Glu | Tyr | Leu | Ala | Arg | Leu | Thr | Phe | Thr | Pro | Thr | Ser | |
| | | 275 | | | | | 280 | | | | | 285 | | | | |
| TGG | GAA | TGG | AAC | TTG | TTC | TGG | ACT | TCA | CCA | GAG | GAG | CCG | GAG | TGC | GAT | 912 |
| Trp | Glu | Trp | Asn | Leu | Phe | Trp | Thr | Ser | Pro | Glu | Glu | Pro | Glu | Cys | Asp | |
| | | 290 | | | | | 295 | | | | | 300 | | | | |
| GTG | TAC | AAG | ACT | TGT | GGG | TCT | TAT | GCT | TAC | TGT | GAC | GTG | AAC | ACA | TCA | 960 |
| Val | Tyr | Lys | Thr | Cys | Gly | Ser | Tyr | Ala | Tyr | Cys | Asp | Val | Asn | Thr | Ser | |
| 305 | | | | | 310 | | | | | 315 | | | | | 320 | |
| CCA | GTG | TGT | AAC | TGT | ATC | CAA | GGT | TTC | AAG | CCC | TTC | AAT | ATG | CAG | CAG | 1008 |
| Pro | Val | Cys | Asn | Cys | Ile | Gln | Gly | Phe | Lys | Pro | Phe | Asn | Met | Gln | Gln | |
| | | | | 325 | | | | | 330 | | | | | 335 | | |
| TGG | GAA | CTG | AGA | GTC | TGG | GCA | GGT | GGG | TGT | ATA | AGG | AGG | ACG | CGG | CTT | 1056 |
| Trp | Glu | Leu | Arg | Val | Trp | Ala | Gly | Gly | Cys | Ile | Arg | Arg | Thr | Arg | Leu | |
| | | | 340 | | | | | 345 | | | | | 350 | | | |
| AGC | TGC | AAT | GGA | GAT | GGT | TTT | ACC | AGG | ATG | AAA | AAT | ATG | AAG | TTG | CCA | 1104 |
| Ser | Cys | Asn | Gly | Asp | Gly | Phe | Thr | Arg | Met | Lys | Asn | Met | Lys | Leu | Pro | |
| | | 355 | | | | | 360 | | | | | 365 | | | | |
| GAA | ACT | ACG | ATG | GCT | ATT | GTC | GAC | CGC | AGT | ATT | GGT | CGG | AAA | GAA | TGT | 1152 |
| Glu | Thr | Thr | Met | Ala | Ile | Val | Asp | Arg | Ser | Ile | Gly | Arg | Lys | Glu | Cys | |
| | 370 | | | | | 375 | | | | | 380 | | | | | |
| AAG | AAG | AGG | TGC | CTT | AGC | GAT | TGT | AAT | TGT | ACC | GCG | TTT | GCA | AAT | GCG | 1200 |
| Lys | Lys | Arg | Cys | Leu | Ser | Asp | Cys | Asn | Cys | Thr | Ala | Phe | Ala | Asn | Ala | |
| 385 | | | | | 390 | | | | | 395 | | | | | 400 | |
| GAT | ATC | CGG | AAT | GGT | GGG | TCG | GGT | TGT | GTG | ATT | TGG | ACA | GGA | GAG | CTT | 1248 |
| Asp | Ile | Arg | Asn | Gly | Gly | Ser | Gly | Cys | Val | Ile | Trp | Thr | Gly | Glu | Leu | |
| | | | | 405 | | | | | 410 | | | | | 415 | | |
| GAG | GAT | ATC | CGG | AAT | TAC | TTT | GAT | GAC | GGT | CAA | GAT | CTT | TAT | GTC | AGA | 1296 |
| Glu | Asp | Ile | Arg | Asn | Tyr | Phe | Asp | Asp | Gly | Gln | Asp | Leu | Tyr | Val | Arg | |
| | | | 420 | | | | | 425 | | | | | 430 | | | |
| TTG | GCT | GCC | GCT | GAT | CTC | GTT | AAA | AAG | AGA | AAC | GCG | AAT | GGG | AAA | ACC | 1344 |
| Leu | Ala | Ala | Ala | Asp | Leu | Val | Lys | Lys | Arg | Asn | Ala | Asn | Gly | Lys | Thr | |
| | | | 435 | | | | | 440 | | | | | 445 | | | |
| ATA | GCG | TTG | ATT | GTT | GGA | GTT | TGT | GTT | CTG | CTT | CTT | ATG | ATC | ATG | TTC | 1392 |
| Ile | Ala | Leu | Ile | Val | Gly | Val | Cys | Val | Leu | Leu | Leu | Met | Ile | Met | Phe | |
| 450 | | | | | 455 | | | | | 460 | | | | | | |

| | | | | | | | | | | | | | | | | |
|---|---|---|---|---|---|---|---|---|---|---|---|---|---|---|---|---|
| TGC | CTC | TGG | AAA | AGG | AAA | CAA | AAG | CGA | GCA | AAA | ACA | ACT | GCA | ACA | TCT | 1440 |
| Cys | Leu | Trp | Lys | Arg | Lys | Gln | Lys | Arg | Ala | Lys | Thr | Thr | Ala | Thr | Ser | |
| 465 | | | | 470 | | | | | 475 | | | | | | 480 | |
| ATT | GTA | AAT | CGA | CAG | AGA | AAC | CAA | GAT | TTG | CTA | ATG | AAC | GGG | ATG | ATA | 1488 |
| Ile | Val | Asn | Arg | Gln | Arg | Asn | Gln | Asp | Leu | Leu | Met | Asn | Gly | Met | Ile | |
| | | | | 485 | | | | | 490 | | | | | 495 | | |
| CTA | TCA | AGC | AAG | AGA | CAG | TTG | CCT | ATA | GAG | AAC | AAA | ACT | GAG | GAA | TTG | 1536 |
| Leu | Ser | Ser | Lys | Arg | Gln | Leu | Pro | Ile | Glu | Asn | Lys | Thr | Glu | Glu | Leu | |
| | | | 500 | | | | | 505 | | | | | 510 | | | |
| GAA | CTT | CCA | TTG | ATA | GAG | TTG | GAA | GCT | GTT | GTC | AAA | GCC | ACC | GAA | AAT | 1584 |
| Glu | Leu | Pro | Leu | Ile | Glu | Leu | Glu | Ala | Val | Val | Lys | Ala | Thr | Glu | Asn | |
| | | 515 | | | | | 520 | | | | | 525 | | | | |
| TTC | TCC | AAT | TGT | AAC | AAA | CTC | GGA | CAA | GGT | GGT | TTC | GGT | ATT | GTT | TAC | 1632 |
| Phe | Ser | Asn | Cys | Asn | Lys | Leu | Gly | Gln | Gly | Gly | Phe | Gly | Ile | Val | Tyr | |
| 530 | | | | | 535 | | | | | 540 | | | | | | |
| AAG | GGT | AGA | TTA | CTT | GAT | GGG | CAA | GAA | ATT | GCG | GTA | AAA | AGG | CTA | TCA | 1680 |
| Lys | Gly | Arg | Leu | Leu | Asp | Gly | Gln | Glu | Ile | Ala | Val | Lys | Arg | Leu | Ser | |
| 545 | | | | | 550 | | | | | 555 | | | | | 560 | |
| AAA | ACG | TCG | GTT | CAA | GGG | ACT | GGT | GAG | TTT | ATG | AAT | GAG | GTG | AGA | TTG | 1728 |
| Lys | Thr | Ser | Val | Gln | Gly | Thr | Gly | Glu | Phe | Met | Asn | Glu | Val | Arg | Leu | |
| | | | | 565 | | | | | 570 | | | | | 575 | | |
| ATC | GCG | AGG | CTT | CAG | CAT | ATA | AAC | CTT | GTC | CGA | ATT | CTT | GGC | TGT | TGC | 1776 |
| Ile | Ala | Arg | Leu | Gln | His | Ile | Asn | Leu | Val | Arg | Ile | Leu | Gly | Cys | Cys | |
| | | | 580 | | | | | 585 | | | | | 590 | | | |
| ATT | GAG | GCA | GAC | GAG | AAG | ATG | CTG | GTA | TAT | GAG | TAT | TTA | GAA | AAT | TTA | 1824 |
| Ile | Glu | Ala | Asp | Glu | Lys | Met | Leu | Val | Tyr | Glu | Tyr | Leu | Glu | Asn | Leu | |
| | | | 595 | | | | | 600 | | | | | 605 | | | |
| AGC | CTC | GAT | TCT | TAT | CTC | TTC | GGA | AAT | AAA | CGA | AGC | TCT | ACG | TTA | AAT | 1872 |
| Ser | Leu | Asp | Ser | Tyr | Leu | Phe | Gly | Asn | Lys | Arg | Ser | Ser | Thr | Leu | Asn | |
| | | 610 | | | | | 615 | | | | | 620 | | | | |
| TGG | AAG | GAC | AGA | TTC | AAC | ATT | ACC | AAT | GGT | GTT | GCT | CGA | GGA | CTT | TTA | 1920 |
| Trp | Lys | Asp | Arg | Phe | Asn | Ile | Thr | Asn | Gly | Val | Ala | Arg | Gly | Leu | Leu | |
| 625 | | | | | 630 | | | | | 635 | | | | | 640 | |
| TAT | CTT | CAT | CAA | GAC | TCA | CGG | TTT | AGG | ATA | ATC | CAC | AGA | GAT | ATG | AAA | 1968 |
| Tyr | Leu | His | Gln | Asp | Ser | Arg | Phe | Arg | Ile | Ile | His | Arg | Asp | Met | Lys | |
| | | | | 645 | | | | | 650 | | | | | 655 | | |
| GTA | AGT | AAC | ATT | TTG | CTT | GAT | AAA | AAT | ATG | ACA | CCA | AAG | ATC | TCG | GAT | 2016 |
| Val | Ser | Asn | Ile | Leu | Leu | Asp | Lys | Asn | Met | Thr | Pro | Lys | Ile | Ser | Asp | |
| | | | 660 | | | | | 665 | | | | | 670 | | | |
| TTT | GGG | ATG | GCC | AGA | ATC | TTT | GCA | AGG | GAC | GAG | ACT | GAA | GCT | AAC | ACA | 2064 |
| Phe | Gly | Met | Ala | Arg | Ile | Phe | Ala | Arg | Asp | Glu | Thr | Glu | Ala | Asn | Thr | |
| | | 675 | | | | | 680 | | | | | 685 | | | | |
| AGG | AAG | GTG | GTC | GGA | ACT | TAC | GGC | TAC | ATG | TCT | CCG | GAG | TAC | GCA | ATG | 2112 |
| Arg | Lys | Val | Val | Gly | Thr | Tyr | Gly | Tyr | Met | Ser | Pro | Glu | Tyr | Ala | Met | |
| | 690 | | | | | 695 | | | | | 700 | | | | | |
| GAT | GGG | GTA | TTC | TCG | GAA | AAA | TCA | GAT | GTT | TTC | AGT | TTT | GGA | GTC | ATT | 2160 |
| Asp | Gly | Val | Phe | Ser | Glu | Lys | Ser | Asp | Val | Phe | Ser | Phe | Gly | Val | Ile | |
| 705 | | | | | 710 | | | | | 715 | | | | | 720 | |
| GTT | CTT | GAA | ATT | GTT | AGT | GGA | AAA | AGG | AAC | AGA | GGA | TTC | TAC | AAC | TTG | 2208 |
| Val | Leu | Glu | Ile | Val | Ser | Gly | Lys | Arg | Asn | Arg | Gly | Phe | Tyr | Asn | Leu | |
| | | | | 725 | | | | | 730 | | | | | 735 | | |
| AAC | CAC | GAA | AAC | AAT | CTT | CTA | AGC | TAT | GTA | TGG | AGT | CAC | TGG | ACG | GAG | 2256 |
| Asn | His | Glu | Asn | Asn | Leu | Leu | Ser | Tyr | Val | Trp | Ser | His | Trp | Thr | Glu | |
| | | | 740 | | | | | 745 | | | | | 750 | | | |
| GGA | AGA | GCG | CTA | GAA | ATT | GTT | GAT | CCA | GTC | ATC | GTA | GAT | TCA | TTG | TCA | 2304 |
| Gly | Arg | Ala | Leu | Glu | Ile | Val | Asp | Pro | Val | Ile | Val | Asp | Ser | Leu | Ser | |
| | | 755 | | | | | 760 | | | | | 765 | | | | |
| TCA | TTA | CCA | GCA | ACC | TTT | CAA | CCA | AAA | GAA | GTT | CTA | AAA | TGC | ATA | CAA | 2352 |
| Ser | Leu | Pro | Ala | Thr | Phe | Gln | Pro | Lys | Glu | Val | Leu | Lys | Cys | Ile | Gln | |
| 770 | | | | | 775 | | | | | 780 | | | | | | |

```
ATT GGT CTC TTG TGT GTT CAA GAA CGT GCA GAG CAT AGA CCA ACG ATG       2400
Ile Gly Leu Leu Cys Val Gln Glu Arg Ala Glu His Arg Pro Thr Met
785             790                 795                         800

TCG TCC GTG GTT TGG ATG CTT GGA AGT GAA GCA ACA GAG ATT CCT GAG       2448
Ser Ser Val Val Trp Met Leu Gly Ser Glu Ala Thr Glu Ile Pro Glu
                805                 810                 815

CCT ACA CCG CCA GGT TAT TCC CTC GGA AGA AGT CCT TAT GAA AAT AAT       2496
Pro Thr Pro Pro Gly Tyr Ser Leu Gly Arg Ser Pro Tyr Glu Asn Asn
            820                 825                 830

CCT TCA TCA AGT AGA CAT TGC GAC GAC GAC GAA TCC TGG ACG GTG AAC       2544
Pro Ser Ser Ser Arg His Cys Asp Asp Asp Glu Ser Trp Thr Val Asn
        835                 840                 845

CAG TAC ACC TGC TCA GAC ATC GAT GCC CGG TAGTACGAAA TCCGTTGAGA         2594
Gln Tyr Thr Cys Ser Asp Ile Asp Ala Arg
850                 855

AAGTTCAGAT AATTAACTAT TGGGGTGACC GGATATTATA AGTGAAAGAA AATAAAATTT     2654

CAATAGTTAA GTTTGTTATT TGATAACCAA ATCTTGTTAT TTCCTGGTGG TGTTGTCATA     2714

TTCGTTTTTC TGAATGAATG TTAAAGTTAT TATTC                                2749
```

( 2 ) INFORMATION FOR SEQ ID NO:2:

( i ) SEQUENCE CHARACTERISTICS:
        ( A ) LENGTH: 858 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Gly Val Arg Lys Thr Tyr Asp Ser Ser Tyr Thr Leu Ser Phe
1               5                   10                  15

Leu Leu Val Phe Phe Val Met Phe Leu Phe His Pro Ala Leu Ser Ile
                20                  25                  30

His Ile Asn Thr Leu Ser Ser Thr Glu Ser Leu Thr Ile Ser Asn Asn
            35                  40                  45

Arg Thr Leu Val Ser Pro Gly Asn Val Phe Glu Leu Gly Phe Phe Arg
        50                  55                  60

Thr Thr Ser Ser Ser Arg Trp Tyr Leu Gly Ile Trp Tyr Lys Asn Leu
65                  70                  75                  80

Pro Tyr Lys Thr Tyr Val Trp Val Ala Asn Arg Asp Asn Pro Leu Ser
                85                  90                  95

Asp Ser Ile Gly Thr Leu Lys Ile Ser Asn Met Asn Leu Val Leu Leu
            100                 105                 110

Asp His Ser Asn Lys Ser Val Trp Ser Thr Asn Leu Thr Arg Gly Asn
        115                 120                 125

Glu Arg Ser Pro Val Val Ala Glu Leu Leu Glu Asn Gly Asn Phe Val
130                 135                 140

Ile Arg Tyr Ser Asn Asn Asn Asn Ala Ser Gly Phe Leu Trp Gln Ser
145                 150                 155                 160

Phe Asp Phe Pro Thr Asp Thr Leu Leu Pro Glu Met Lys Leu Gly Tyr
                165                 170                 175

Asp Arg Lys Lys Gly Leu Asn Arg Phe Leu Thr Ala Trp Arg Asn Ser
            180                 185                 190

Asp Asp Pro Ser Ser Gly Glu Ile Ser Tyr Gln Leu Asp Thr Gln Arg
        195                 200                 205

Gly Met Pro Glu Phe Tyr Leu Leu Lys Asn Gly Val Arg Gly Tyr Arg
210                 215                 220
```

```
Ser  Gly  Pro  Trp  Asn  Gly  Val  Arg  Phe  Asn  Gly  Ile  Pro  Glu  Asp  Gln
225            230                      235                           240

Lys  Leu  Ser  Tyr  Met  Val  Tyr  Asn  Phe  Thr  Asp  Asn  Ser  Glu  Glu  Ala
                    245                250                      255

Ala  Tyr  Thr  Phe  Arg  Met  Thr  Asp  Lys  Ser  Ile  Tyr  Ser  Arg  Leu  Ile
               260                 265                           270

Ile  Ser  Asn  Asp  Glu  Tyr  Leu  Ala  Arg  Leu  Thr  Phe  Thr  Pro  Thr  Ser
          275                 280                      285

Trp  Glu  Trp  Asn  Leu  Phe  Trp  Thr  Ser  Pro  Glu  Glu  Pro  Glu  Cys  Asp
     290                      295                 300

Val  Tyr  Lys  Thr  Cys  Gly  Ser  Tyr  Ala  Tyr  Cys  Asp  Val  Asn  Thr  Ser
305                      310                 315                           320

Pro  Val  Cys  Asn  Cys  Ile  Gln  Gly  Phe  Lys  Pro  Phe  Asn  Met  Gln  Gln
                    325                 330                           335

Trp  Glu  Leu  Arg  Val  Trp  Ala  Gly  Gly  Cys  Ile  Arg  Arg  Thr  Arg  Leu
               340                      345                           350

Ser  Cys  Asn  Gly  Asp  Gly  Phe  Thr  Arg  Met  Lys  Asn  Met  Lys  Leu  Pro
          355                 360                      365

Glu  Thr  Thr  Met  Ala  Ile  Val  Asp  Arg  Ser  Ile  Gly  Arg  Lys  Glu  Cys
     370                      375                 380

Lys  Lys  Arg  Cys  Leu  Ser  Asp  Cys  Asn  Cys  Thr  Ala  Phe  Ala  Asn  Ala
385                      390                 395                           400

Asp  Ile  Arg  Asn  Gly  Gly  Ser  Gly  Cys  Val  Ile  Trp  Thr  Gly  Glu  Leu
               405                      410                           415

Glu  Asp  Ile  Arg  Asn  Tyr  Phe  Asp  Asp  Gly  Gln  Asp  Leu  Tyr  Val  Arg
               420                 425                      430

Leu  Ala  Ala  Ala  Asp  Leu  Val  Lys  Lys  Arg  Asn  Ala  Asn  Gly  Lys  Thr
               435                 440                      445

Ile  Ala  Leu  Ile  Val  Gly  Val  Cys  Val  Leu  Leu  Leu  Met  Ile  Met  Phe
450                      455                 460

Cys  Leu  Trp  Lys  Arg  Lys  Gln  Lys  Arg  Ala  Lys  Thr  Thr  Ala  Thr  Ser
465                 470                      475                           480

Ile  Val  Asn  Arg  Gln  Arg  Asn  Gln  Asp  Leu  Met  Asn  Gly  Met  Ile
                    485                 490                      495

Leu  Ser  Ser  Lys  Arg  Gln  Leu  Pro  Ile  Glu  Asn  Lys  Thr  Glu  Glu  Leu
               500                 505                      510

Glu  Leu  Pro  Leu  Ile  Glu  Leu  Glu  Ala  Val  Val  Lys  Ala  Thr  Glu  Asn
               515                 520                      525

Phe  Ser  Asn  Cys  Asn  Lys  Leu  Gly  Gln  Gly  Gly  Phe  Gly  Ile  Val  Tyr
     530                      535                 540

Lys  Gly  Arg  Leu  Leu  Asp  Gly  Gln  Glu  Ile  Ala  Val  Lys  Arg  Leu  Ser
545                      550                 555                           560

Lys  Thr  Ser  Val  Gln  Gly  Thr  Gly  Glu  Phe  Met  Asn  Glu  Val  Arg  Leu
                    565                 570                           575

Ile  Ala  Arg  Leu  Gln  His  Ile  Asn  Leu  Val  Arg  Ile  Leu  Gly  Cys  Cys
               580                 585                      590

Ile  Glu  Ala  Asp  Glu  Lys  Met  Leu  Val  Tyr  Glu  Tyr  Leu  Glu  Asn  Leu
          595                      600                 605

Ser  Leu  Asp  Ser  Tyr  Leu  Phe  Gly  Asn  Lys  Arg  Ser  Ser  Thr  Leu  Asn
     610                      615                 620

Trp  Lys  Asp  Arg  Phe  Asn  Ile  Thr  Asn  Gly  Val  Ala  Arg  Gly  Leu  Leu
625                      630                 635                           640

Tyr  Leu  His  Gln  Asp  Ser  Arg  Phe  Arg  Ile  Ile  His  Arg  Asp  Met  Lys
               645                 650                      655
```

| | | | | | | | | | | | | | |
|---|---|---|---|---|---|---|---|---|---|---|---|---|---|
|Val|Ser|Asn|Ile<br>660|Leu|Leu|Asp|Lys|Asn<br>665|Met|Thr|Pro|Lys|Ile<br>670|Ser|Asp|
|Phe|Gly|Met<br>675|Ala|Arg|Ile|Phe|Ala<br>680|Arg|Asp|Glu|Thr|Glu<br>685|Ala|Asn|Thr|
|Arg|Lys<br>690|Val|Val|Gly|Thr|Tyr<br>695|Gly|Tyr|Met|Ser|Pro<br>700|Glu|Tyr|Ala|Met|
|Asp<br>705|Gly|Val|Phe|Ser|Glu<br>710|Lys|Ser|Asp|Val|Phe<br>715|Ser|Phe|Gly|Val|Ile<br>720|
|Val|Leu|Glu|Ile|Val<br>725|Ser|Gly|Lys|Arg|Asn<br>730|Arg|Gly|Phe|Tyr|Asn<br>735|Leu|
|Asn|His|Glu|Asn<br>740|Asn|Leu|Leu|Ser|Tyr<br>745|Val|Trp|Ser|His|Trp<br>750|Thr|Glu|
|Gly|Arg|Ala|Leu<br>755|Glu|Ile|Val|Asp<br>760|Pro|Val|Ile|Val|Asp<br>765|Ser|Leu|Ser|
|Ser|Leu<br>770|Pro|Ala|Thr|Phe|Gln<br>775|Pro|Lys|Glu|Val|Leu<br>780|Lys|Cys|Ile|Gln|
|Ile<br>785|Gly|Leu|Leu|Cys|Val<br>790|Gln|Glu|Arg|Ala|Glu<br>795|His|Arg|Pro|Thr|Met<br>800|
|Ser|Ser|Val|Val|Trp<br>805|Met|Leu|Gly|Ser|Glu<br>810|Ala|Thr|Glu|Ile|Pro<br>815|Glu|
|Pro|Thr|Pro|Pro<br>820|Gly|Tyr|Ser|Leu|Gly<br>825|Arg|Ser|Pro|Tyr|Glu<br>830|Asn|Asn|
|Pro|Ser|Ser<br>835|Ser|Arg|His|Cys|Asp<br>840|Asp|Asp|Glu|Ser|Trp<br>845|Thr|Val|Asn|
|Gln|Tyr<br>850|Thr|Cys|Ser|Asp|Ile<br>855|Asp|Ala|Arg| | | | | | |

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( i x ) FEATURE:
        ( A ) NAME/KEY: misc_recomb
        ( B ) LOCATION: 1..26

( x i ) SEQUENCE DESCRIPTION: SEQ ID NO:3:

GTCAAGCTTG TGGCAAAGTT TCGATT                2 6

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: YES ( i x ) FEATURE:
        ( A ) NAME/KEY: misc_feature (B) LOCATION: 1..29

(x i) SEQUENCE DESCRIPTION: SEQ ID NO:4:

GTCAAGCTTC TGACATAAAG ATCTTGACC                                                29

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: YES (i v) ANTI-SENSE: NO (v i) ORIGINAL SOURCE:
        (A) ORGANISM: Brassica napus
        (B) STRAIN: oleifera W1

(x i) SEQUENCE DESCRIPTION: SEQ ID NO:5:

AGTAACGATG AGTATTTGGC                                                          20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:6:

CATATTGAAG GGCTTGAAAC                                                          20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:7:

TCCGGAATTA CTTTGATGAC                                                          20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO -continued (iv) ANTI-SENSE: YES (xi) SEQUENCE DESCRIPTION: SEQ ID NO:8:

GAAAGGTTGC TGGTAATGAT                    20

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Brassica napus
        (B) STRAIN: oleifera W1

(xi) SEQUENCE DESCRIPTION: SEQ ID NO:9:

GATCCAGATC TCGAGAAGCT TTTTTTTTTT TTTTTT                    36

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..24

(xi) SEQUENCE DESCRIPTION: SEQ ID NO:10:

GCGGATCCAG ATCTCGAGAA GCTT                    24